(12) United States Patent
Beith

(10) Patent No.: US 7,682,389 B2
(45) Date of Patent: Mar. 23, 2010

(54) CARDIAC VALVE FEATURING A PARABOLIC FUNCTION

(75) Inventor: Jason Gordon Beith, Parkland, FL (US)

(73) Assignee: AorTech International PLC, Bellshill, Lanarkshire (GB)

( * ) Notice: Subject to any disclaimer, the term of this patent is extended or adjusted under 35 U.S.C. 154(b) by 0 days.

(21) Appl. No.: 10/524,612

(22) PCT Filed: Mar. 22, 2004

(86) PCT No.: PCT/GB2004/001244

§ 371 (c)(1),
(2), (4) Date: May 15, 2006

(87) PCT Pub. No.: WO2004/082536

PCT Pub. Date: Sep. 30, 2004

(65) Prior Publication Data

US 2006/0241744 A1     Oct. 26, 2006

(30) Foreign Application Priority Data

Mar. 20, 2003 (GB) ................................ 0306472.2
Aug. 16, 2003 (GB) ................................ 0319321.6

(51) Int. Cl.
*A61F 2/24* (2006.01)
(52) U.S. Cl. .................................................. 623/2.17
(58) Field of Classification Search ................. 623/1.26, 623/2.17, 2.12, 2.14, 2.18, 2.19; 427/2.24
See application file for complete search history.

(56) References Cited

U.S. PATENT DOCUMENTS

| 4,222,126 A | 9/1980 | Boretos et al. ................... 3/1.5 |
| 4,265,694 A | 5/1981 | Boretos et al. .............. 156/242 |
| 4,364,127 A | 12/1982 | Pierce et al. ..................... 3/1.5 |
| 4,473,423 A * | 9/1984 | Kolff .......................... 156/245 |
| 4,731,074 A | 3/1988 | Rousseau et al. ................ 623/2 |
| 4,888,009 A | 12/1989 | Lederman et al. ............... 623/2 |
| 5,358,518 A | 10/1994 | Camilli .......................... 623/2 |
| 5,376,113 A | 12/1994 | Jansen et al. .................... 623/2 |

(Continued)

FOREIGN PATENT DOCUMENTS

EP     0 193 987     2/1986

(Continued)

OTHER PUBLICATIONS

G.Cacciola et al. "A Stentless Fibre-Reinforced Aortic Valve Prosthesis," Journal of Biomechanics, vol. 33, Issue 5, May 2000, pp. 521-530.*

(Continued)

*Primary Examiner*—William H. Matthews
*Assistant Examiner*—Jonathan R Stroud
(74) *Attorney, Agent, or Firm*—Drinker Biddle & Reath LLP

(57) ABSTRACT

There is provided an artificial cardiac or heart valve, more particularly a flexible leaflet heart valve used to replace natural aortic or pulmonary valves of the heart in which the leaflet geometry is defined by a parabolic function and a method of manufacturing said artificial cardiac valves. In addition, there is provided leaflets which have geometry defined by a parabolic function.

8 Claims, 20 Drawing Sheets

U.S. PATENT DOCUMENTS

| | | | |
|---|---|---|---|
| 5,393,858 A | 2/1995 | Meijs et al. | 528/61 |
| 5,403,912 A | 4/1995 | Gunatillake et al. | 528/425 |
| 5,500,016 A | 3/1996 | Fisher | 623/2 |
| 5,562,729 A | 10/1996 | Purdy et al. | 623/2 |
| 5,653,749 A | 8/1997 | Love et al. | 623/2 |
| 5,800,527 A | 9/1998 | Jansen et al. | 623/2 |
| 6,086,612 A | 7/2000 | Jansen | 623/2.17 |
| 6,165,215 A | 12/2000 | Rottenberg et al. | 623/2.12 |
| 6,171,335 B1 | 1/2001 | Wheatley et al. | 623/2.17 |
| 6,283,995 B1 | 9/2001 | Moe et al. | 623/2.19 |
| 6,375,679 B1* | 4/2002 | Martyn et al. | 623/2.12 |
| 6,613,086 B1 | 9/2003 | Moe et al. | |
| 2002/0082687 A1* | 6/2002 | Moe | 623/2.12 |
| 2002/0138138 A1* | 9/2002 | Yang | 623/2.18 |
| 2003/0125804 A1 | 7/2003 | Kruse et al. | 623/2.1 |

FOREIGN PATENT DOCUMENTS

| | | |
|---|---|---|
| EP | 0 402 036 | 5/1990 |
| WO | WO 93/18721 | 9/1993 |
| WO | WO 97/41808 | 11/1997 |
| WO | WO 98/32400 | 7/1998 |
| WO | WO9966863 | 12/1999 |
| WO | WO 00/62716 | 10/2000 |
| WO | WO 01/41679 A1 | 6/2001 |
| WO | WO0141679 | 6/2001 |
| WO | WO02100301 | 12/2002 |

OTHER PUBLICATIONS

"Arc Length and Surface Area," University of British Columbia web document. http://www.ugrad.math.ubc.ca/coursedoc/math101/notes/moreApps/arclength.html, accessed Aug. 3, 2007.*

Bernacca, et al., G.M.,: "Durability and Function of a Polyurethane Heart Valve After Six Months In Vivo." *Artificial Organs, Official Journal of the International Society for Artificial Organs*. 1999, vol. 23, No. 7.

Bernacca, et al., G.M.: "In Vitro Function and Durability Assessment of a Novel Polyurethane Heart Valve Prosthesis." *Artificial Organs, Official Journal of the International Society for Artificial Organs*. Sep. 1996, vol. 20, No. 9.

Bernacca, et al., G.M.: "In Vitro Function and Durability of a Polyurethane Heart Valve: Material Considerations." *The Journal of Heart Valve Disease*. Sep. 1996, vol. 5, No. 5.

Bernacca, et al., G.M.: "Polyurethane heart valve durability: effects of leaflet thickness and material." *The International Journal of Artificial Organs*. Jun. 1997, vol. 20, No. 6.

Bernacca, et al., G.M.: "Polyurethane heart valves: Fatigue failure, calcification, and polyurethane structure." *Journal of Biomedical materials Research*. Mar. 5, 1997, vol. 34, No. 3.

Mackay, et al., T.G.: "New polyurethane heart valve prosthesis: design, manufacture and evaluation." *Biomaterials, incorporating Clinical Material*. 1996, vol. 17, No. 19.

Wheatley, et al, D.J..: "Polyurethane: material for the next generation of heart valve prostheses?" *European Journal of Cardio-Thoracic Surgery*. Apr. 2000, vol. 17, No. 4.

* cited by examiner

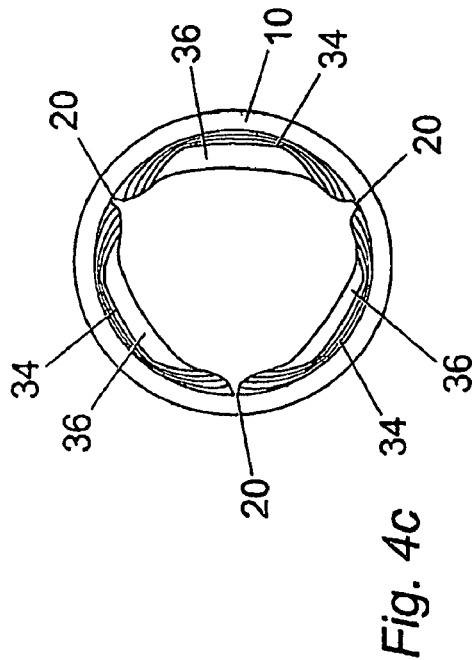
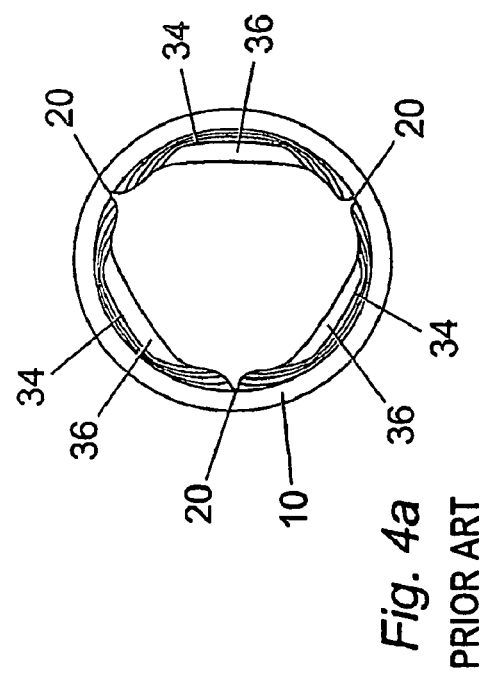
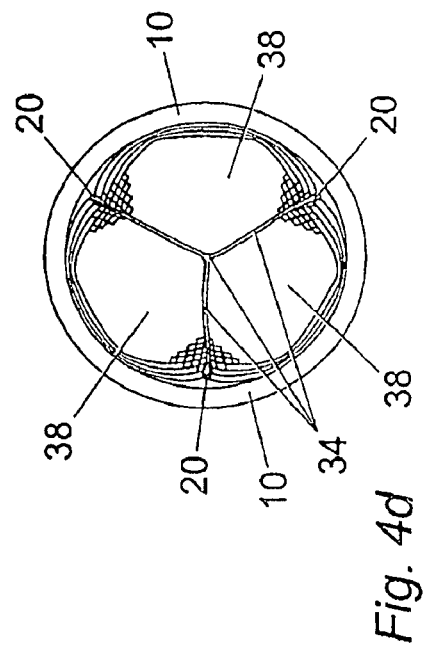
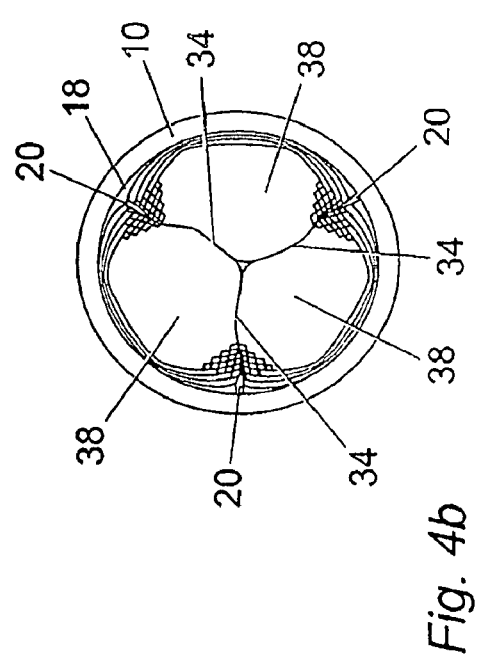
Fig. 4a PRIOR ART
Fig. 4b PRIOR ART
Fig. 4c
Fig. 4d

CARDIAC VALVE FEATURING A PARABOLIC FUNCTION

This Application is the U.S. National Phase Application of PCT International Application No PCT/GB2004/001244 filed Mar. 22, 2004.

DESCRIPTION OF THE RELATED ART

The present invention relates to artificial cardiac or heart valves, more particularly to flexible leaflet heart valves which are used to replace natural aortic or pulmonary valves of the heart.

Ideally artificial heart valves should work in a similar fashion to natural heart valves in that when blood flows in a particular direction the valve adopts an open position to permit blood flow through it, whereas when blood tries to flow in the opposite direction the valve adopts a closed position preventing the flow of blood in the reverse direction through the valve (regurgitation).

Natural heart valves use thin flexible tissue leaflets as the closing members. In the closed position the leaflets are arranged such that each leaflet contacts its neighbour. This arrangement serves to close the valve and prevent the back flow of blood through the valve. In the open position the leaflets separate from each other and move radially towards the inner walls of the blood vessel in which the valve is located. This open configuration of the valve permits the flow of blood through the valve.

A number of artificial cardiac valves have been produced which comprise leaflets which open and close in a similar fashion to natural valve leaflets. However, although the artificial valves work in a similar manner to the natural valves, the geometries of the leaflets differ due to the properties of the materials used in the construction of the synthetic heart valves.

A number of factors have to be considered when designing artificial heart valves of similar design to natural heart valves. These include the pressure gradient required to open and close the leaflets of the valve, regurgitation, blood handling and durability of the valve.

The leaflets of both natural and synthetic heart valves must be capable of withstanding a high back pressure across the valve when they are in the closed position, yet be capable of opening with a minimum of pressure across the valve in the forward direction of blood flow.

This is necessary to ensure correct operation of the valve even when blood flow is low. Further the valve should open quickly and as wide as possible when blood flows in the desired direction. The maximum orifice of the valve in the open position is generally dictated by the width of the valve.

In order to minimise closing regurgitation (reverse blood flow through the closing valve) in the closed position of the valve, the free edges of the leaflets should come together to form a seal to minimise the reverse flow of blood.

The valve design and the materials used for valve construction should minimise the activation of both the coagulation system and platelets. The flow of blood through the valve should avoid exposing blood to either regions of high shear or relative stasis.

Conventional heart valves typically comprise an annular frame disposed perpendicular to the blood flow. The annular frame generally has three posts extending in the downstream direction defining three generally U-Shaped openings or scallops between the posts. The leaflets are attached to the frame between the posts along the edges of the scallops and are unattached at the free edges of the leaflets adjacent to the downstream ends of the posts.

International Patent Application WO 98/32400 entitled "Heart Valve Prosthesis" discloses a cardiac valve design, using closed leaflet geometry, comprising essentially a trileaflet valve with leaflets moulded in a geometry derived from a sphere towards the free edge and a cone towards the base of the leaflets. The spherical surface, defined by its radius, is intended to provide a tight seal when the leaflets are under back pressure, with ready opening provided by the conical segment, defined by its half-angle, at the base of the leaflets.

International Patent Application WO 01/41679 discloses a heart valve wherein the leaflets have been designed to facilitate wash out of the whole leaflet orifice including the area close to the frame posts. This application teaches that stresses are highest in the region of the commisures where loads are transmitted to the stent, but they are reduced when the belly of the leaflet is as low as practicable in the closed valve. To ensure a belly in the leaflet, the above application indicates that there must be sufficient material in the leaflet.

In addition, in order to be suitable for implantation, synthetic valves should be sufficiently durable such that they are clinically functional for at least 20 years. Durability of the synthetic leaflets depends on the materials from which the leaflets are constructed and also the stresses to which the leaflets are subjected during use. However, although improvements have been made to cardiac valves over recent years, problems still exist with artificial valves. Although several materials have suitable hydrodynamic properties, many valves constructed using materials with apparently suitable hydrodynamic properties nevertheless fail during use, due to fatigue caused by the repeated stresses of cycling from a closed to an open position.

The present inventor have surprisingly found that, by using leaflets with parabolic configuration in cross section, stresses of the leaflets can be reduced and hence the lifespan of the valve may be improved.

BRIEF SUMMARY OF THE INVENTION

It is an aim of the present invention to provide an improved cardiac valve prosthesis.

Thus, according to the present invention, there is provided a cardiac valve prosthesis comprising:

a frame and at least two flexible leaflets;

wherein the frame comprises an annular portion which, in use, is disposed substantially perpendicular to the blood flow, the frame having first and second ends, one of the ends defining at least two scalloped edge portions separated and defined by at least two posts, each leaflet being attached to the frame along a scalloped edge portion and being movable between an open and a closed position, each of the at least two leaflets having a blood inlet side, a blood outlet side and at least one free edge, the at least two leaflets being in a closed position when fluid pressure is applied to the outlet side such that the at least one free edge of a first leaflet is urged towards the at least one free edge of a second or further leaflet, and the at least two leaflets being in an open position when fluid pressure is applied to the blood inlet side of the at least two leaflets such that the at least one free edge of the first leaflet is urged away from the at least one free edge of the second or further leaflet;

wherein, in a first plane perpendicular to the blood flow axis, the length of each leaflet in a circumferential direction (XY) between the posts at any position along the longitudinal axis (Z) of a post is defined by a parabolic function.

It is understood that reference to a parabolic function includes reference to any pseudotrigonmetric, pseudoelliptical, smooth function or table of values that describe a geometry which is substantially parabolic.

The use of a pseudo function to describe a parabolic function will be clear to one skilled in the art.

Preferably the parabolic function defining the length of a leaflet in the circumferential direction (XY) between the posts at any position along the longitudinal axis (Z) of a post is defined by $$Y_z = \left(\frac{4R}{L_z^2}\right) x \cdot (L_z - x)$$

Wherein
$Y_z$=Y offset at a particular co-ordinate X and Z
R=parabolic maximum
$L_z$=straight line distance between a first post and a second post of the frame at a height Z
x=distance from origin of post towards another post
wherein the length of the parabola can be determined by $$\text{Length} = \int_0^l \sqrt{1 + \left(\frac{dy}{dx}\right)^2} \, dx$$

Preferably at least one correction factor can be applied to the measured lengths of for example $L_z$ or R to take into account changes in the dimensions of the frame or material of the leaflet during the cycling of the cardiac valve between an open and closed position. For example, such changes, in the dimensions may be, but are not limited to, inward movement of the posts of the prosthesis on closure of the valve, stretch in leaflet material on closure of the valve, or movement in the notional point of coincidence of the leaflets. It will be clear to the skilled man how to determine the correction factor required in view of the frame and leaflet material selected.

Preferably the correction factor is positive, negative or zero.

The materials chosen to form the frame and the leaflets of the prosthesis and the design of the frame will influence to what extent the prosthesis, including both the frame and the leaflets, yields to the forces to which the prosthesis is subjected during valve closure and opening. For example, typically, inward movement of the posts of the prosthesis occurs on closure of the valve due to the force of the backward flow of blood on the leaflet. This typically occurs to a greater extent at the tips of the posts than where the posts meet the frame. A correction factor is preferably included in the determination of the XY lengths of the leaflet at each height in Z to compensate for this movement in the frame.

Preferably the cardiac valve prosthesis of the first aspect of the invention comprises three leaflets.

In an embodiment of the valve comprising three leaflets, one end of the frame of the cardiac valve prosthesis defines at least three scalloped edge portions separated by at least three posts, wherein each leaflet is attached to the frame along a corresponding scalloped edge portion.

In such embodiments, preferably the three posts are rotationally symmetrically distributed around the circumference of the frame.

Preferably the frame is a collapsible stent. This may be advantageous as a collapsible stent may be delivered to a patient by percutaneous delivery. In a preferred embodiment of the valve wherein the frame is a collapsible stent, the collapsible stent may be moved from a collapsed to an erect position using an inflatable balloon when the stent is suitably located in the patient.

The inventor has provided an improved cardiac valve prosthesis by determining an advantageous leaflet geometry. Indeed, a leaflet having such geometry comprises an independent aspect of the present invention.

According to a second aspect of the invention there is provided a valve leaflet for use in the valve according to the first aspect of the invention, wherein the length of the leaflet in a circumferential direction (XY) between the lateral edges at any position along the lateral edge for attachment to the post is defined by a parabolic function.

Preferably the valve leaflet is a cardiac valve leaflet for use in a cardiac valve prosthesis, more preferably the cardiac valve prosthesis of the first aspect of the invention.

As discussed above a parabolic function includes any pseudotrigonmetric, pseudoelliptical, smooth function or table of values that describe a geometry which is substantially parabolic.

Preferably the parabolic function defining the length of a leaflet in the circumferential direction (XY) between the posts at any position along the longitudinal axis (Z) of a post is defined by $$Y_z = \left(\frac{4R}{L_z^2}\right) x \cdot (L_z - x)$$

Wherein
$Y_z$=Y offset at a particular co-ordinate X and Z
R=parabolic maximum
$L_z$=straight line distance between a first post and a second post of the frame at a height Z
x=distance from origin of post towards another post
wherein the length of the parabola can be determined by $$\text{Length} = \int_0^l \sqrt{1 + \left(\frac{dy}{dx}\right)^2} \, dx$$

Preferably at least one correction factor can be applied to the measured lengths of for example $L_z$ or R to take into account changes in the dimensions of the frame or material of the leaflet during the cycling of the cardiac valve between an open and closed position.

Preferably the correction factor is a positive, negative or zero.

The leaflets are preferably formed from any biostable and biocompatible material.

Preferably the leaflets are formed from Elasteon.

Preferably the leaflet has different thicknesses along a cross section defined by the intersection of a plane perpendicular to the blood flow axis.

More preferably the thickness of the cross section of the leaflet in the XY plane, defined by the intersection of a plane perpendicular to the blood flow axis, changes gradually and substantially continuously from a thickest portion where the leaflet is conjoined to the frame to a thinnest portion at the midpoint of the XY plane of the leaflet.

The leaflets of a valve as described above have a top and bottom. In a preferred embodiment, wherein the valve is a cardiac valve prosthesis of the first aspect of the invention, the bottom of the leaflet is attached to the scalloped portion and the top of the leaflet defines the free edge.

Preferably the free edge of the leaflet is shaped to increase the length of the free edge of the leaflet relative to the length of the leaflet in the XY direction.

A valve leaflet of the second aspect of the invention may be manufactured as part of the valve prosthesis or may alternatively be formed independently and then attached to the valve once formed.

Typically changing the diameter of the valve or height of the posts of the frame affects the calculation of leaflet geometry i.e. the length of the leaflets in the XY direction required to obtain suitable closure of the valve. Conventionally, geometric scaling is employed to determine the leaflet geometry for different diameters of valves, but this technique lacks accuracy.

An advantage of the parabolic function described herein to determine the XY length of the leaflet of a cardiac valve is that the function can be used irrespective of valve diameter or the height of the posts of the frame to determine suitable leaflet geometry and do not require the use of geometric scaling.

Therefore functions disclosed by the present application which describe length in the circumferential direction (XY) of a leaflet e.g. the leaflet geometry optimised for a 27 mm inside diameter of stent can be used to describe the length in the circumferential direction (XY) leaflet geometry for a stent of different diameter e.g. 17 mm inside diameter stent.

This makes the design and manufacture of valves of different diameters which comprise the leaflets of the second aspect of the invention more convenient.

Preferably the free edge of the leaflet is shaped such that in the longitudinal direction (Z) the free edge of at least one leaflet is parabolic.

The parabola can be in either direction. However if the parabola extends away from the frame preferably the maximum height of the parabola is 0 μm to 500 μm more preferably 0 μm to 100 μm, even more preferably 0 μm to 50 μm higher than the notional straight line between the ends of the parabola.

More preferably the free edge of at least one leaflet is parabolic in the longitudinal direction toward the scalloped edge portion of the frame such that the maximum depth of the parabola is between 50 μm to 1000 μm, more preferably 50 μm to 500 μm, even more preferably 50 μm to 100 μm lower than the notional straight line between the ends of the parabola.

The inventor has surprisingly shown that by making the free edge of valve leaflets parabolic, the stress and strain characteristics of the leaflet at the free edge are improved.

In particular embodiments the parabolic shape of the free edge may be produced by trimming of the free edge.

The valve of the first aspect of the invention can be manufactured by any suitable method as known in the art for example by adapting the method as disclosed in WO 01/41679 or WO 02/100301. During manufacture of a cardiac valve prosthesis it is preferable if the leaflets are cast in a shape which minimises the stresses in the leaflet during cycling of the valve between the open and closed position. Preferably, the leaflets are formed in a neutral position, not fully open or closed. In addition, as will be appreciated by those skilled in the art, in a fully closed position the free edge of the leaflets will be touching or almost touching each other making manufacture of the leaflet difficult. Once the length in XY of the leaflet, in respect of the frame at a height Z has been determined the cast shape of the leaflet can be defined to allow manufacture of the leaflet on a forming element.

A preferred method of manufacture of the leaflets of the first aspect of the invention has been developed by the inventor. Indeed this preferred method provides a further independent aspect to the invention.

According to a third aspect there is provided a method of manufacturing a cardiac valve prosthesis wherein the method comprises;

providing a forming element having at least two leaflet-forming surfaces wherein the forming surfaces are such that the length in the circumferential direction (XY) of the leaflet-forming surface is defined by a parabolic function, engaging the forming element with a frame, applying a coating over the frame and the engaged forming element, the coating binding to the frame, the coating over the leaflet-forming surfaces forming at least two flexible leaflets, the at least two flexible leaflets having a length in the circumferential direction (XY) defined by a parabolic function and a surface contour such that when the first leaflet is in a neutral position an intersection of the first leaflet with at least one plane perpendicular to the blood flow axis forms a wave, disengaging the frame from the forming element.

The coating is preferably a synthetic polymer material, more preferably a synthetic resin or plastics material.

As indicated above, when casting the leaflets, it is desirable to keep the leaflets in a neutral position and not touching each other. This is achievable by casting the leaflets in a wave configuration. The leaflets are in a neutral position intermediate to the open and closed position in the absence of fluid pressure being applied to the leaflets.

The shape of the leaflet forming surfaces on which the leaflets are cast is preferably defined by a wave function. The wave function is thus applied to the leaflet(s) to aid production of the leaflets whose length in an XY direction has been determined.

The shape of the leaflet forming surfaces on which the leaflets are cast may be defined by a first wave having a first frequency. The first wave may be a sinusoidal wave.

Alternatively, the shape of the leaflet forming surfaces on which the leaflets are cast may be defined by at least two waves of differing frequencies, which together form a composite wave.

A composite wave can be more complicated than a single wave function. This provides a greater range of leaflet cast shapes, wherein the XY lengths of the leaflet at each height Z is defined by a parabolic function or the like, in which the leaflets may be manufactured.

Preferably the wave defining the leaflet forming surfaces and thus the cast shape of a leaflet is asymmetric about the vertical mid plane parallel to and intersecting the blood flow axis of the leaflets when in use.

Alternatively, the wave defining the leaflet forming surfaces and thus the cast shape of a leaflet is asymmetric about the vertical mid plane parallel to and intersecting the blood flow axis of the leaflets.

In preferred embodiments the method further comprises trimming the free edge of at least one fo the leaflets formed. In particularly preferred embodiments the method further comprises trimming the free edge to a parabolic shape.

It is preferred that the frame comprises three posts. Preferably the number of leaflet forming surfaces is equal to the number of posts.

In the method of the invention the coating may be applied to the frame in any suitable way known in the art, for example using dip moulding, conventional injection moulding, reaction injection moulding or compression moulding.

Dip moulding can be used to form surgical implants of relatively complex shapes. Typically dip moulding is achieved by dipping a forming element into synthetic polymer material, which may include polymer resin or plastic material, removing the forming element from the synthetic polymer material and allowing the resultant coating of synthetic polymer material on the forming element to dry or cure. The moulded article is then removed from the forming element.

A disadvantage of conventional dip moulding, as described above, is that during the moulding of intricate shapes, bubbles of air frequently become trapped in cavities or recesses of the mould template. These bubbles of air remain trapped in the moulded article when the article is cured and give rise to holes or pits in the moulded article rendering the moulded article unsuitable for use. Another problem encountered is that of providing an even coating for articles of complex geometry. For example, precision coating is essential for producing surgical implants of intricate shapes such as prosthetic heart valves. In particular, the problems of bubbles and applying an even coating are encountered when more viscous moulding materials are used for moulding.

These problems with dip moulding can be minimised by using inverted dip moulding.

The coating may be applied over the frame by a method of inverted dip moulding comprising the steps:
  submerging a forming element in a moulding solution;
  inverting said forming element whilst in the moulding solution; and
  isolating the forming element from the moulding solution so that the coating thus formed on the forming element can be dried or cured.

Inversion of the forming element whilst in the moulding solution reduces the number of bubbles formed in the coating. Furthermore, such apparatus enables more efficient use of moulding solution and lends itself advantageously to batch processing.

In embodiments in which inverted dip moulding is used, the method may comprise the steps of:
(i) attaching a forming element to a platform;
(ii) sealing a housing to said platform to form a closed chamber;
(iii) filling said closed chamber with moulding solution until the forming element is submerged;
(iv) inverting said closed chamber;
(v) isolating the coated forming element from the moulding solution.

The coated forming element can be isolated from the moulding solution by either breaking the seal and removing the platform, for example by raising the platform and thus the forming element out of the solution, or by draining the moulding solution from the closed chamber via outlet means.

An apparatus for use in aspects of this invention in which inverted dip moulding is used comprises:
  at least one platform adapted to hold at least one forming element;
  at least one housing having an open end adapted to fit over said at least one forming element;
  sealing means for reversibly sealing said housing to said platform to form a closed chamber suitable for holding a moulding solution;
  means for inverting said closed chamber;
  closeable inlet means for introducing a moulding solution into the closed chamber; and
  closeable outlet means for releasing a moulding solution from the housing.

In particular embodiments of the manufacture of the cardiac valve leaflet, in particular, coating of the frame to form the leaflets, inverted dip moulding and cutting or trimming of the leaflets, the forming element is comprised of at least two portions wherein portions are releasably attached to each other.

Preferably releasable attachment of the at least two portions of the forming element is provided by a screw.

In a particular embodiment a first portion of the forming element is a cardiac valve frame mounting portion and a second portion is a base portion. The base portion may be releasably attachable to the inverted dip moulding apparatus.

The coating may be heated prior and/or during moulding to aid movement of the material around the forming element. This may be achieved by for example heating at least a part of the moulding apparatus is heated such that it heats the moulding solution.

Preferably the synthetic polymer material is biostable and biocompatible.

More preferably the synthetic polymer material is Elasteon.

As described above, the inventor has found that providing a parabolic shape to the free edge is advantageous.

The parabolic shape may be formed during the coating process or alternatively subsequent to manufacture of the leaflets. It has been found that it may be advantageous to cut the leaflets after formation. For example, as discussed above, it may be advantageous to trim the free edge of a leaflet, e.g. to form a parabolic shape.

To date, conventional blades have been used to cut moulded devices such as cardiac valves and leaflets formed from synthetic polymer material. However, these conventional blades become blunted over a relatively short period of time, leading to the production of moulded devices with a poor surface finish on the cut edge.

To provide a high quality finish to a cut edge of the leaflet with minimal disruptions to the cutting process to replace cutting blades it has been determined that an ultrasonic cutting device may be used.

The leaflets may be cut using an ultrasonic cutting device comprising
(i) an ultrasonic transducer;
(ii) an elongate blade; and
(iii) attachment means to enable detachable attachment of the blade to the transducer so that, in operation, the transducer causes the blade to vibrate in a direction along the longitudinal axis of the blade.

It has been found that, for a given ultrasonic frequency, by altering the dimensions of an elongate blade, optimal operation of the cutting device can be achieved. Reducing the amplitude of vibrations perpendicular to the plane of the blade results in a cleaner cut. It has been found that by having a blade of this particular construction precise cutting of synthetic polymer material, for example, resin and plastics materials can be achieved. The cutting device of the present invention is particularly suitable for cutting acetyls, polyurethane and polymeric materials.

Preferably the blade has a width to length ratio of between 0.1 to 0.4. By width means the width of the widest part of the blade and by length is meant the length of the longest part of the blade.

Preferably the elongate blade has a length in the range of 20 to 30 mm, a thickness in the range of 0.5 to 2 mm and a width in the range of 2 to 10 mm. More preferably the width of the blade is between 5 and 8 mm.

Preferably the ultrasonic transducer or motor produces vibrational energy at a frequency of 15 Hz.

The blade is provided with a terminal end, which is the end furthest away from the transducer, which terminal end may have a single cutting edge and this may be rounded in shape. Preferably the blade has a plurality of cutting edges. Preferably the blade has cutting edges along its longitudinal sides which form a point at the terminal end of the blade, for example in an arrowhead configuration. Preferably, the longitudinal sides are arcuate in shape. In one embodiment the blade is needle-shaped. Preferably the blade is symmetrical in shape about its longitudinal axis.

The blade may be constructed from any suitable material such as stainless steel, mild steel or ceramic material. Preferably the blade is constructed from a ceramic material. This is advantageous as ceramic material is harder than steel and remains cooler during operation of the cutting device as there is less heat transfer to the blade.

Preferably the cutting apparatus further comprises (i) a stylus for guiding the blade of the cutting device on the surface of the article to be cut which stylus comprises a rotatable ball bearing mounted on an arm; and (ii) attachment means for attaching the stylus to the ultrasonic cutting device.

The stylus is positioned so that, in operation, the ball bearing is in contact with the surface of the article to be cut. Preferably the rotatable ball bearing is positioned above, but not in contact with, the terminal end of the blade. Preferably the outer most part of the rotatable ball bearing does not extend to the outermost tip of the terminal end of the blade so that, while the ball bearing is in contact with the article to be cut, the cutting edge of the terminal end of the blade penetrates the article by a constant predetermined amount. This results in a consistent and precise cut with each part of the article experiencing the same exposure to the cutting edge of the blade.

The attachment means for attaching the stylus to the ultrasonic cutting device may form part of means for mounting the cutting device on a mounting table. The means for mounting the cutting device on a mounting table may further comprise means such as a 3-axis drive unit as known in the art in which each arm of the drive unit can move linearly in three directions perpendicular to each other such that the ultrasonic cutting device can be suitably positioned relative to the article to be cut.

Preferably the article to be cut is mountable on the drive unit, for example the forming element on which the cardiac valve leaflet to be cut is formed may be mountable on the drive unit.

A cardiac valve leaflet may be cut using an ultrasonic vibrating blade comprising the steps of, (i) positioning a blade relative to the heart valve leaflet to be cut;

(ii) vibrating the blade;

(iii) moving the heart valve leaflet to be cut relative to the vibrating blade or alternatively moving the vibrating blade relative to the heart valve leaflet to be cut so that the blade cuts the heart valve leaflet to the required shape.

The heart valve leaflet may be mountable on the mounting table while it is on the forming element on which it was moulded.

As described herein, an advantage of the valve of the first aspect of the invention is that stresses experienced by the leaflets during the cycling from the closed to the open positions are minimised.

By minimising the stresses present in the leaflets of the valve during cycling from the closed to the open position and back to the closed position the lifetime of the synthetic leaflets is likely to be increased.

The present inventor has determined that fatigue failures of previous synthetic valve are due to bending stresses. In particular, the inventor has determined that bending stresses affect synthetic polymer valve material differently to non-synthetic valve material.

Indeed, the present inventor has determined that by considering the stresses and strains of the leaflets during cycling of the valve an optimal leaflet geometry can be determined. This principle may be applied to the design of other valves.

Accordingly, in a further independent aspect of the invention there is provided a method of designing a cardiac valve prosthesis comprising the steps, a) providing a model of a heart valve comprising a frame and at least two flexible leaflets, b) generating loads experienced by at least one cardiac valve leaflet in use and applying these to the model, c) determining the stress distribution of the leaflet, d) changing the circumferential length of the leaflet in XY for any position in Z, e) determining the new stress distribution of the leaflet, f) repeating steps D and E to minimise local stress concentrations in the leaflet.

In preferred embodiments of this aspect of the invention, the cardiac valve prosthesis is a cardiac valve prosthesis of a first aspect of the invention.

In a particularly preferred embodiment the model comprises three flexible leaflets.

Preferably the method further includes the step of adjusting the model to account for factors which influence the stress distribution of the leaflet during the cycling of the cardiac valve between an open and closed position.

More preferably, where the leaflets are formed from synthetic polymer material, the method further includes the step of adjusting the model to account for factors depending on the synthetic polymer material of the leaflet which influence the stress distribution of the leaflet during the cycling of the cardiac valve between an open and closed position.

Preferably the length of the leaflet in the circumferential direction (XY) between the posts at any position along the longitudinal axis (Z) of a post is defined by a parabolic function and at least one correction factor. Preferably the correction factor is used to compensate for at least one of, but not limited to; inward movement of the posts of the prosthesis on closure of the valve, stretch in leaflet material on closure of the valve, or movement in the notional point of coincidence of the leaflets.

Such correction factors are advantageous as they allow the determination of the XY length of the leaflet to take into account factors which effect the XY length of the leaflets required for closure of the valve. For example, inward movement of the posts of the prosthesis occurs on closure of the valve, due to the force of the backward flow of blood on the leaflet. This typically occurs to a greater extent at the tips of the posts than where the posts meet the frame. By providing a correction factor in the determination of the XY lengths of the leaflet at each height in Z to compensate for this movement the leaflet length can be determined to minimise bending stresses, in particular buckling of the leaflet.

The free edge of the leaflet of the cardiac valve is particularly subject to stress and strain.

Preferably the method further comprises the step of providing different shapes and lengths of the free edge of a leaflet.

This is advantageous as it enables the effect of trimming the leaflet to particular shapes, for example parabolic, to be determined.

Preferred aspects of the invention apply to each of the other aspects mutatis mutandis.

BRIEF DESCRIPTION OF THE DRAWINGS

An embodiment of the present invention will now be described, by way of example only with reference to the accompanying drawings wherein;

FIG. 4a is a plan view of a prior art trileaflet heart valve in a fully open position;

FIG. 4b is a plan view of a prior art trileaflet heart valve as shown in FIG. 4a in a fully closed position;

FIG. 4c is a plan view of an embodiment of a trileaflet heart valve according to the present invention in a fully open position;

FIG. 4d is a plan view of an embodiment of a trileaflet heart valve according to the present invention as shown in FIG. 4c in a fully closed position;

FIG. 14a shows a sectional view of an inverted dipping apparatus prior to moulding;

FIG. 14b shows a sectional view of an inverted dip moulding apparatus post moulding;

DETAILED DESCRIPTION OF THE INVENTION

As previously discussed, a number of designs have been suggested for use in cardiac heart valves to ensure that the heart valves have sufficient leaflet material such that the valve is capable of opening as wide as possible to the maximum orifice of the valve, and that such opening requires as little energy as possible and further that regurgitation of blood through the valve is minimised.

In order to minimise the regurgitation of blood it has been suggested that the free edge of the valve is spherical in geometry to ensure that the free leaflet edges are able to come together and seal against one another.

U.S. Pat. No. 5,500,016 discloses a leaflet defined by the equation:

$$z^2 + y^2 = 2RL(x-g) - \alpha(x-g)^2$$

to describe the geometry of the leaflets. As Z, defines the shape of the leaflet in the blood flow axis and as Z is defined as $z^2$ then a leaflet defined by the above would have a spherical geometry in the axis parallel to blood flow. International Patent Application WO 98/32400 discloses that spherical surfaces at the leaflet edges seal more effectively than planar or conical surfaces. International Application WO 01/41679 discloses that stresses are highest in the region of the comissures where loads are transmitted to the stent, but they are reduced when the belly of the leaflet is as low as practicable in the closed valve.

In addition, International Application WO 98/32400 also suggests that it is advantageous to provide a spherical portion of leaflet adjacent to the base of the leaflet as it confers advantages in the stress distribution when the valve is closed and pressure is greater downstream than upstream.

Thus, the prior art teaches that leaflets of heart valves should have considerable excess material in the vertical axis Z, parallel to the blood flow to enable a suitable seal to be achieved at the free edge of the leaflet and to reduce the stress present in the leaflet during open and closing.

Figure 1A:
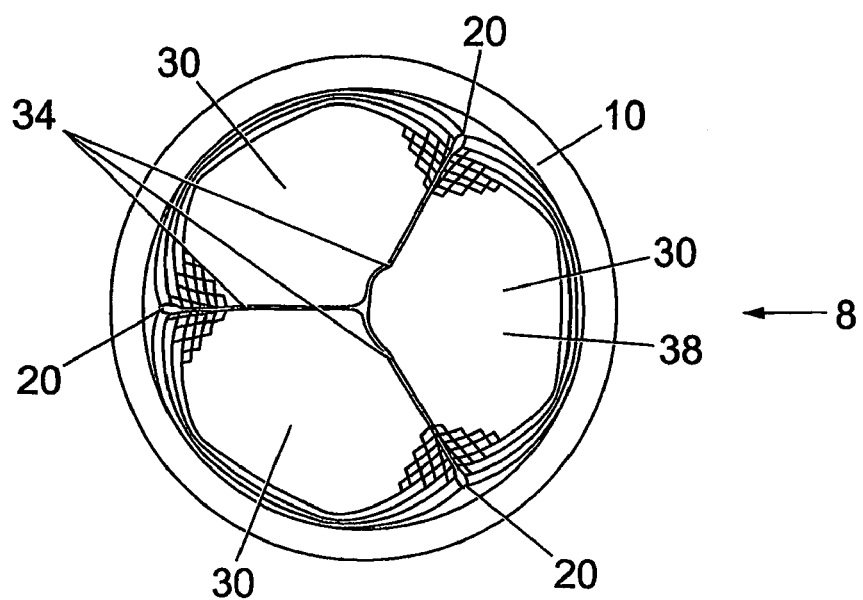
FIG. 1a is a plan view of a trileaflet heart valve in the closed position.
Figure 1B:
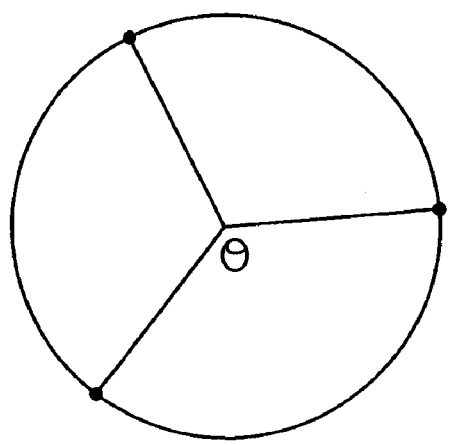
FIGS. 1b, 1c and 1d show plan views of heart valves with 3, 4 or 5 posts in which full closure of the valve is achieved.
Figure 1C:
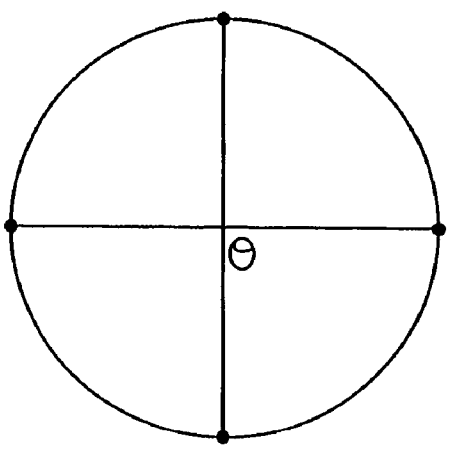
Figure 1D:
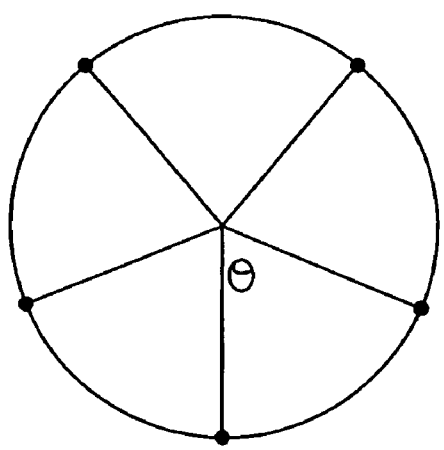

As shown in FIGS. 1b, 1c and 1d, the use of a frame comprising 3, 4 or 5 posts induces different angles θ in the valve leaflets, to ensure a close fitting tight seal of the leaflets, which minimises regurgitation of blood through the valve. As the number of posts increases, the smaller the angle θ and the more bent the leaflets are at a particular point. In cycling between the open and closed position, the valve will undergo considerable flexing, particularly at angle θ. The smaller the angle θ, the greater the stress experienced by the valve at this point and the more the likely the valve is to fail due to stress.

The material properties of tissue, which has low stress at low and moderate strain means tissue valves are more able to cope with such flexing than synthetic materials. Synthetic materials typically have different stress to strain relationships than tissue and higher stress is typically experienced by these materials at low and moderate strains. This means that flexing is more likely to cause damage to leaflets constructed from synthetic material than tissue material.

Previous valve designs have been largely based on tissue valves and have not taken account of the different material properties of synthetic material, particularly synthetic polymer material.

In contrast to previous designs and teaching concerning valve construction, which was driven by the supposed need to obtain a close fitting seal of the leaflets, particularly at the free edge, the leaflets of the valves of the present invention were designed to minimise the stress experienced by the leaflet during cycling between the open and closed position.

To reduce the sharp curvature, which promotes stress points at specific points along the free edge, the length of the free edge (XY) of the leaflet was determined using a parabolic function. The parabolic length of the free edge can be determined by using the distances between the posts of the frame where the free edge is conjoined to the posts and the parabolic maximum.

Figure 1E:
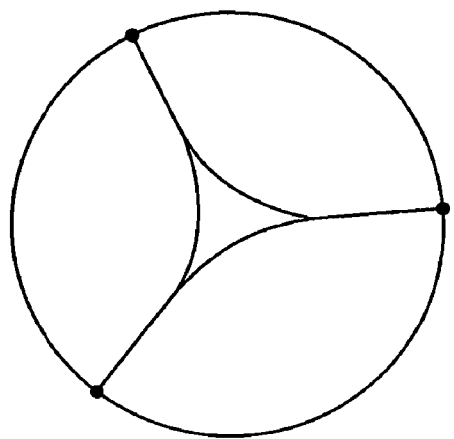
FIGS. 1e, 1f and 1g show plan views of 3, 4 and 5 posted heart valves in which the length XY of the free edge of the leaflets is defined by a parabolic function.
Figure 1F:
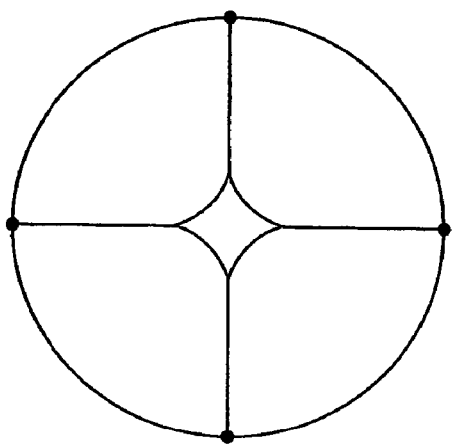
Figure 1G:
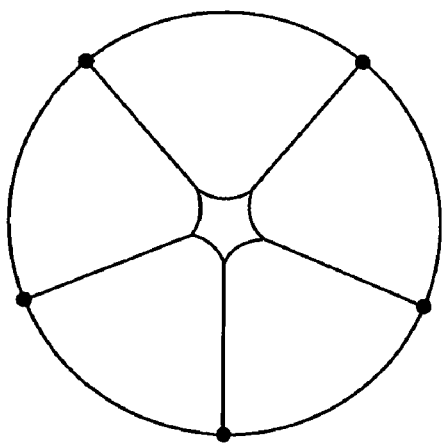

As shown in FIGS. 1e, 1f and 1g the use of a parabolic shape at the free edge results in a gentler curvature of the leaflets and enables the length of the material along the free edge to be determined from a knowledge of the frame dimensions. However, this design, contrary to previous teaching, does not necessarily allow close fitting to be achieved between the leaflets at all points along the free edge. However, surprisingly, the seal obtained between the leaflets using a parabolic or like function was found to be sufficient to minimise regurgitation of blood through the valve to the required degree for the valve to be effective.

The determination of the length XY at the free edge of the leaflet is important to ensure that closure of the leaflets is achieved and to minimise the excess material of the leaflets at the free edge such that the free edges of the leaflets do not fold over each other in the closed position.

In addition to allowing determination of the length of XY at the free edge of the valve, the present application also allows determination of the XY lengths of the leaflets at all points in Z by using a parabolic function to determine the shape of the leaflets at all points in Z.

Figure 5A:
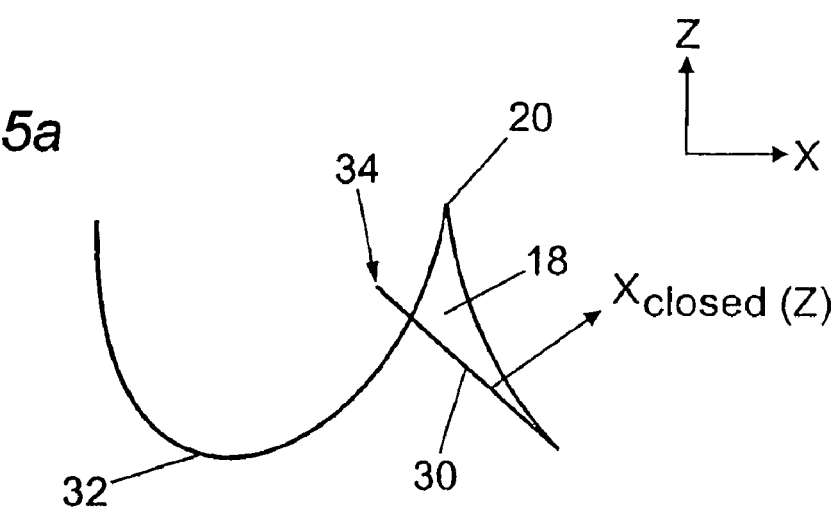
FIG. 5a is a cross section of the valve as shown in FIG. 2a along line 3-3.
Figure 5B:
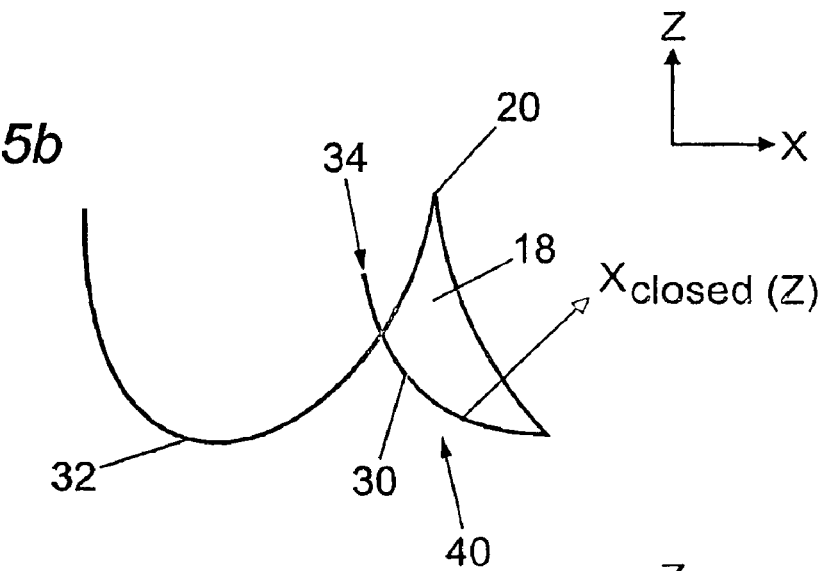
FIG. 5b is a cross section of the prior art valve as shown in FIG. 2b along line 3-3.
Figure 5C:
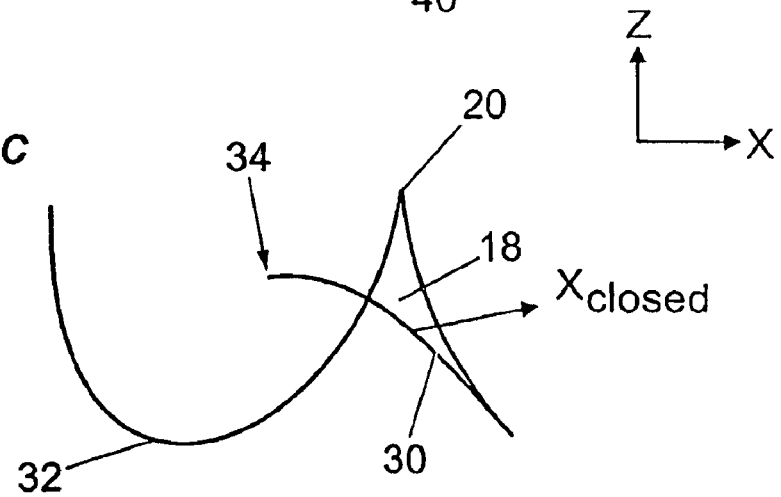
FIG. 5c is a cross section of a valve with a sigmoidal shaped leaflet in Z.

As shown in FIGS. 5a, 5b and 5c, in the closed position, the leaflet can be substantially linear (FIG. 5a), have excess material such that a belly forms (FIG. 5b) or have reduced XY lengths of the leaflet towards the base such that the leaflet forms a generally sigmoidal shape (FIG. 5c). In both FIGS. 5b and 5c the XY lengths of the leaflet and thus the leaflet shape would be determined using a non-continuous function.

The inventor has determined the belly in the valve as shown in FIG. 5b would create increased stress in the belly region. Further, it has been deterimed that, as illustrated in FIG. 5c, a reduction of material in XY towards the base of the posts promotes an increase in the stress concentration at the portion of the leaflets towards the free edge.

By determining the lengths XY of the leaflet as a parabolic function or the like at each point in Z, such that the XY lengths in Z vary as a continuous function, localised stress concentrations can be minimised and a more uniform stress distribution across the leaflet achieved.

Figure 2A:
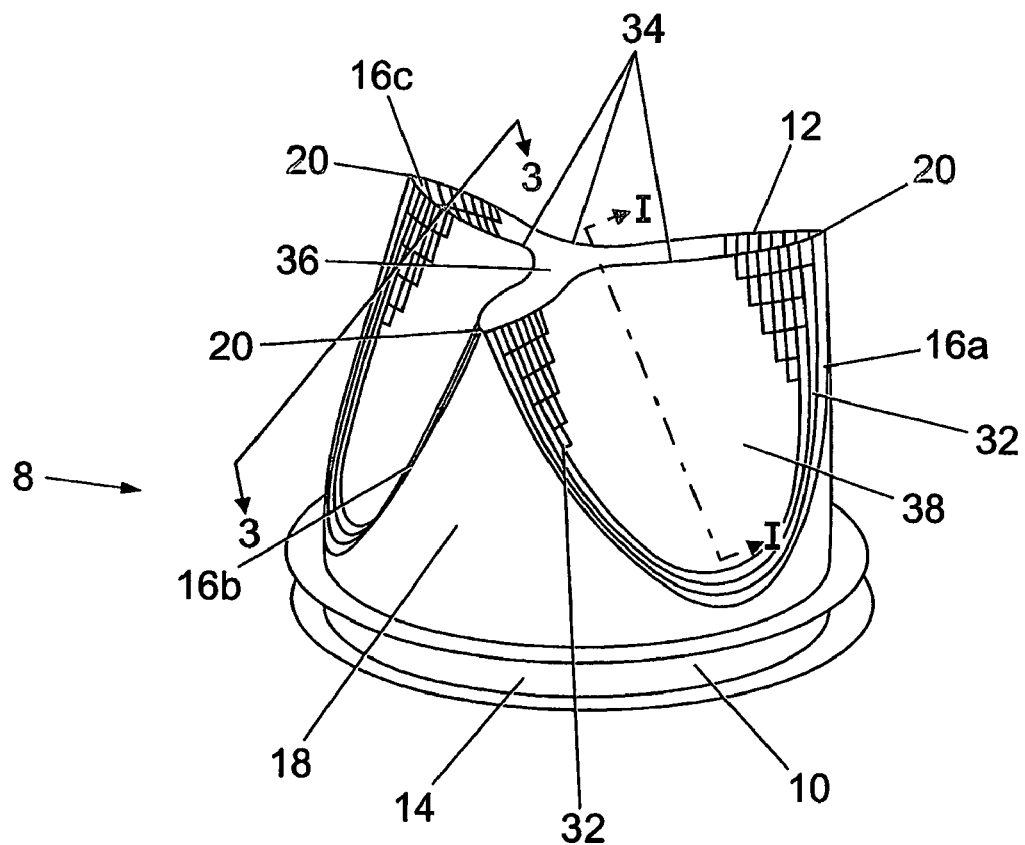
FIG. 2a is a perspective view of an embodiment of a trileaflet heart valve of the present invention in a semi-closed position.

As shown in FIGS. 1a and 2a, a preferred embodiment of the heart valve prosthesis 8 of the present invention comprises a stent or frame 10 which is substantially cylindrical. The frame has a first end 12 and second end 14. The first end 12 comprises three scalloped edge portions 16a, 16b and 16c separated by three posts 18, each post having a tip 20. The cardiac valve further comprises three leaflets 30. Each leaflet 30 has a fixed edge 32 joined to a respective scalloped edge 16a, 16b or 16c of the frame 10 and a free edge 34 which extends substantially between the tips 20 of the posts 18.

The leaflets 30 are configured to be movable from an open to a closed position and from a closed to open position. In an aortic position (when the prosthesis is positioned at the site of the aortic valve), the leaflets 30 have a blood inlet side 36 and a blood outlet side 38 and are in the closed position when fluid pressure is applied to the outlet side 38 i.e. by the blood of the aortic artery and in the open position when fluid pressure is applied to the inlet side 36 i.e. by the blood of the ventricle. The leaflets are in a neutral position intermediate to the open and closed position in the absence of fluid pressure being applied to the leaflets.

Where the valve is being used in a mitral position, between the left atrium and left ventricle of the heart, the orientation of the valve is opposite to that described above such that blood flow from the left atrium moves the leaflets to an open position, the leaflets opening towards the left ventricle to allow blood to flow into the left ventricle. Back pressure from blood flow from the left ventricle towards the left atrium causes the mitral valve to close to minimise regurgitation.

In FIG. 5b which is a sectional view along line 3-3 illustrating the closed position of a leaflet of a valve of the prior art, a 'belly' portion 40 exists in the mid portion of the leaflet. This 'belly' portion between the free edge and the central portion of the leaflet causes leaflets of the prior art to have a double curvature, a curve in XY and a curve in Z. Further, the 'belly' shape 40 causes leaflets of the prior art to be almost concave in shape when viewed in cross section along the vertical midplane of the leaflet.

As shown in FIG. 5a, which is a sectional view of the valve of the present invention along line 3-3 as shown in FIG. 2a, no 'belly' is present in the leaflets and in Z the leaflet in the closed position is substantially linear.

The conventional design including a 'belly' portion was previously favoured as it was thought to maximise sealing of the valve at the free edge and minimise regurgitation.

However, the double curvature, which comprises curvature in XY plane and in Z plane results in excess leaflet material at both the open and closed position which promotes the formation of a bubble or buckle 50 in the leaflet material (as shown in FIG. 11) during movement from a closed to open position.

Figure 2B:
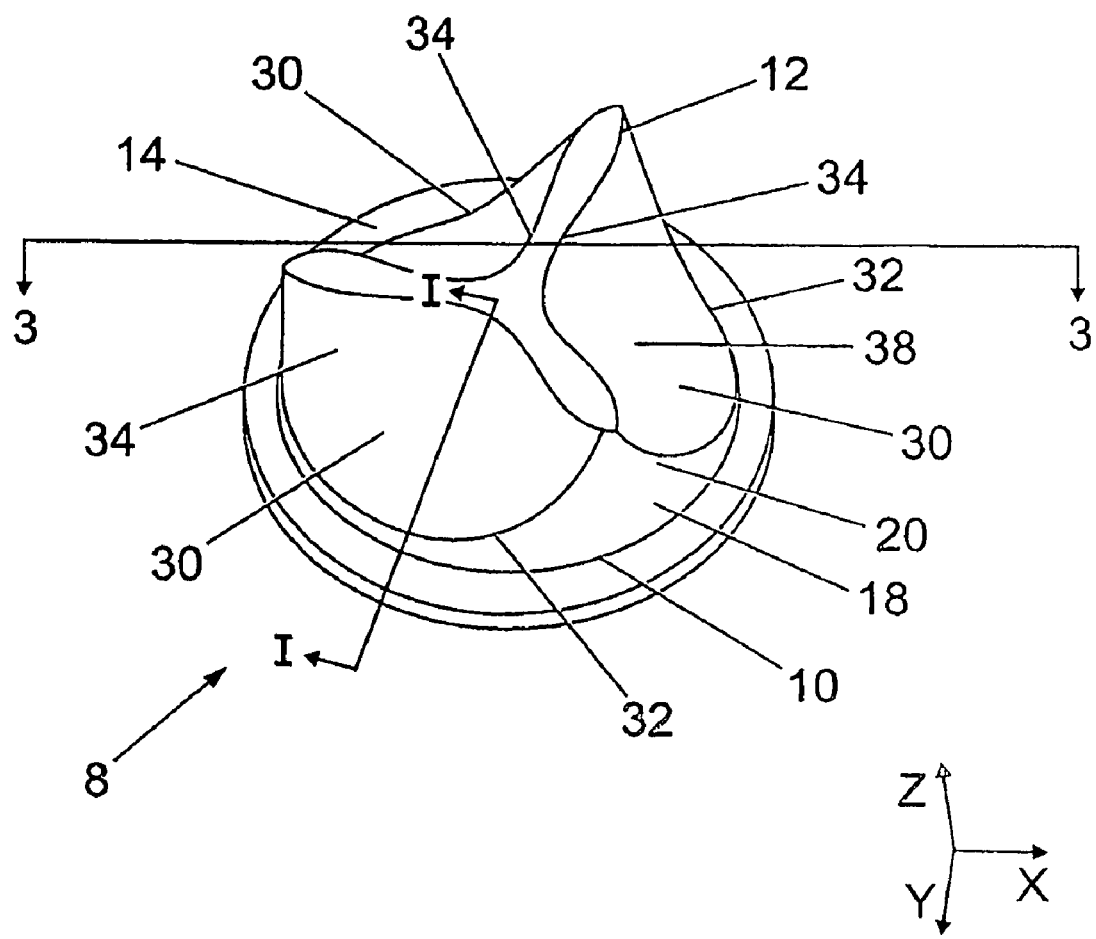
FIG. 2b is a perspective view of a prior art trileaflet heart valve in a semi-closed position.
Figure 3:
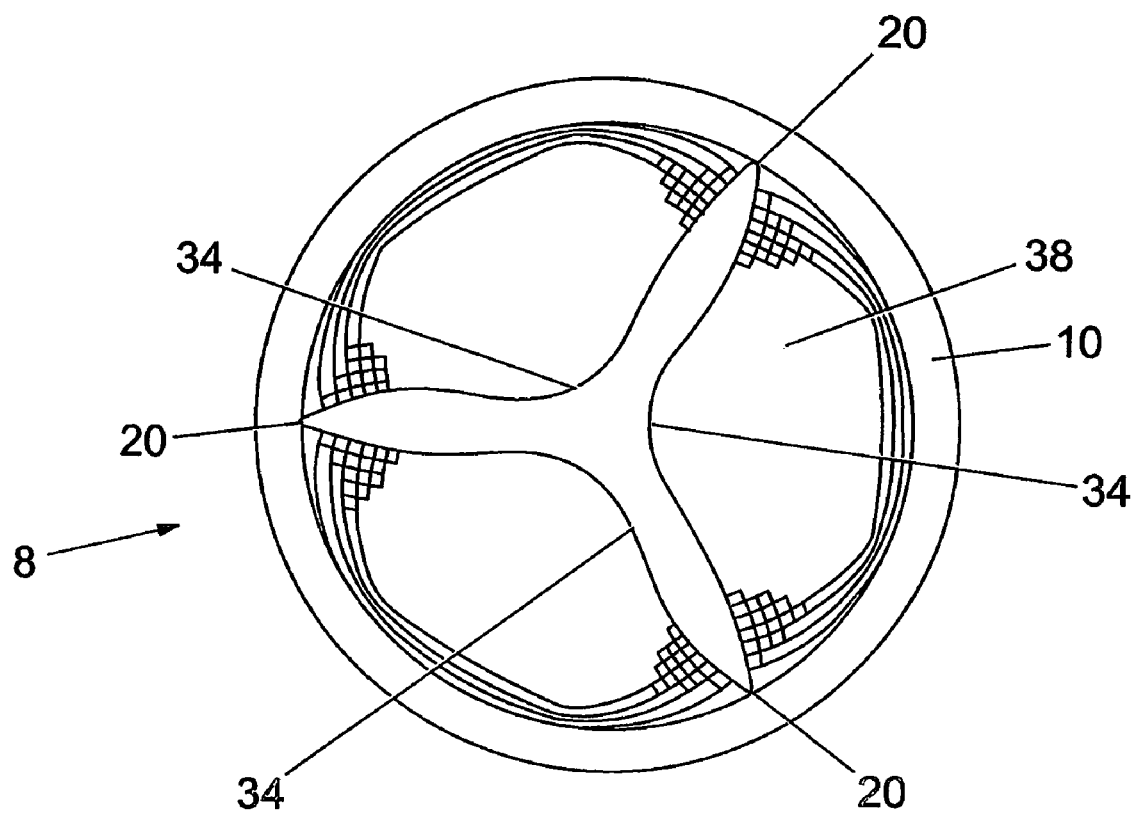
FIG. 3 is a plan view of an embodiment of a trileaflet heart valve of the present invention in a semi-closed position.
Figure 7A:
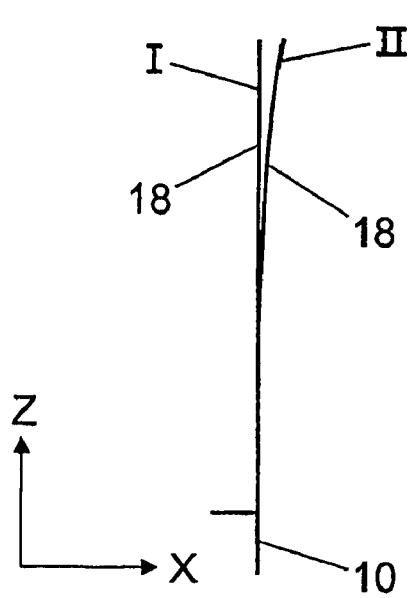
FIG. 7a shows a partial cross section of a post of an embodiment of a trileaflet heart valve of the present invention in the open position (II) and the closed position (I) of the valve.
Figure 7B:
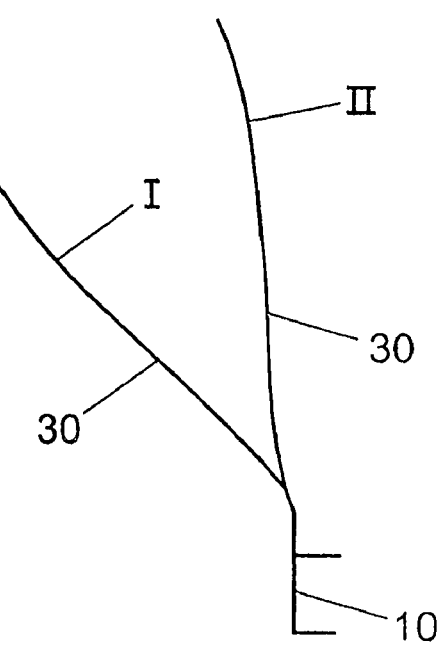
FIG. 7b shows a partial cross section of an embodiment of a leaflet of the present invention along the vertical midplane in the open position (II) and closed position (I) of the valve.
Figure 7C:
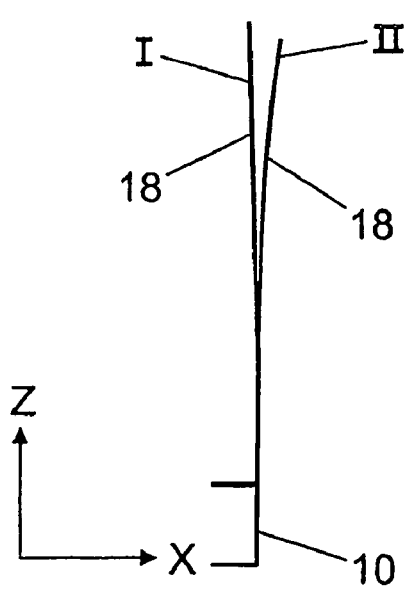
FIG. 7c shows a partial cross section of a post of a prior art valve in the open position (II) and closed position (I) of the valve.
Figure 7D:
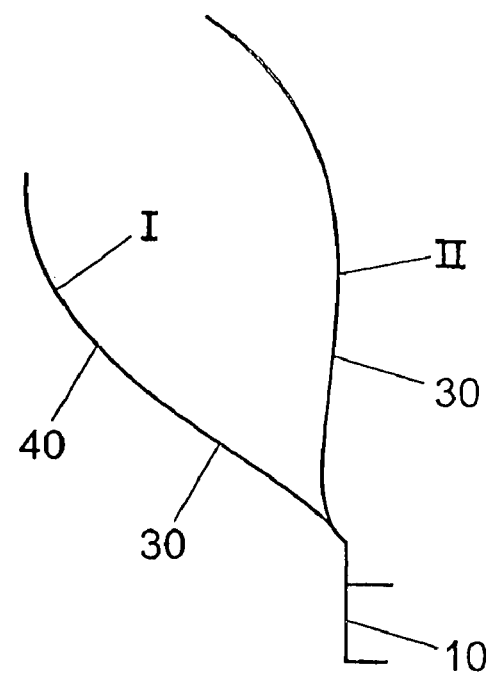
FIG. 7d shows a partial cross section of a leaflet of a prior art valve along the vertical midplane in the open (II) and closed (I) position of the valve.

This excess material is shown most clearly by comparing FIG. 7d which shows a cross section of the valve along the vertical midplane (line I-I of FIG. 2b) of the leaflet 30 parallel to the blood flow axis in a prior art leaflet with FIG. 7b which shows a cross section along the vertical midplane (line I-I of FIG. 2a) of a leaflet of the present invention. This comparison clearly shows that the leaflet 30 of the valve of the present invention does not display a belly region 40.

Indeed the cross section shown in FIG. 7b indicates that the leaflet shape of the present invention is substantially linear in the vertical direction in both the open and closed valve positions.

To determine the circumferential length of material in XY to remove the 'belly' 40 observed in prior art leaflets, the length in the circumferential direction (XY) of the leaflet for any position in z must be determined, which still allows suitable opening and closure of the valve.

Figure 6:
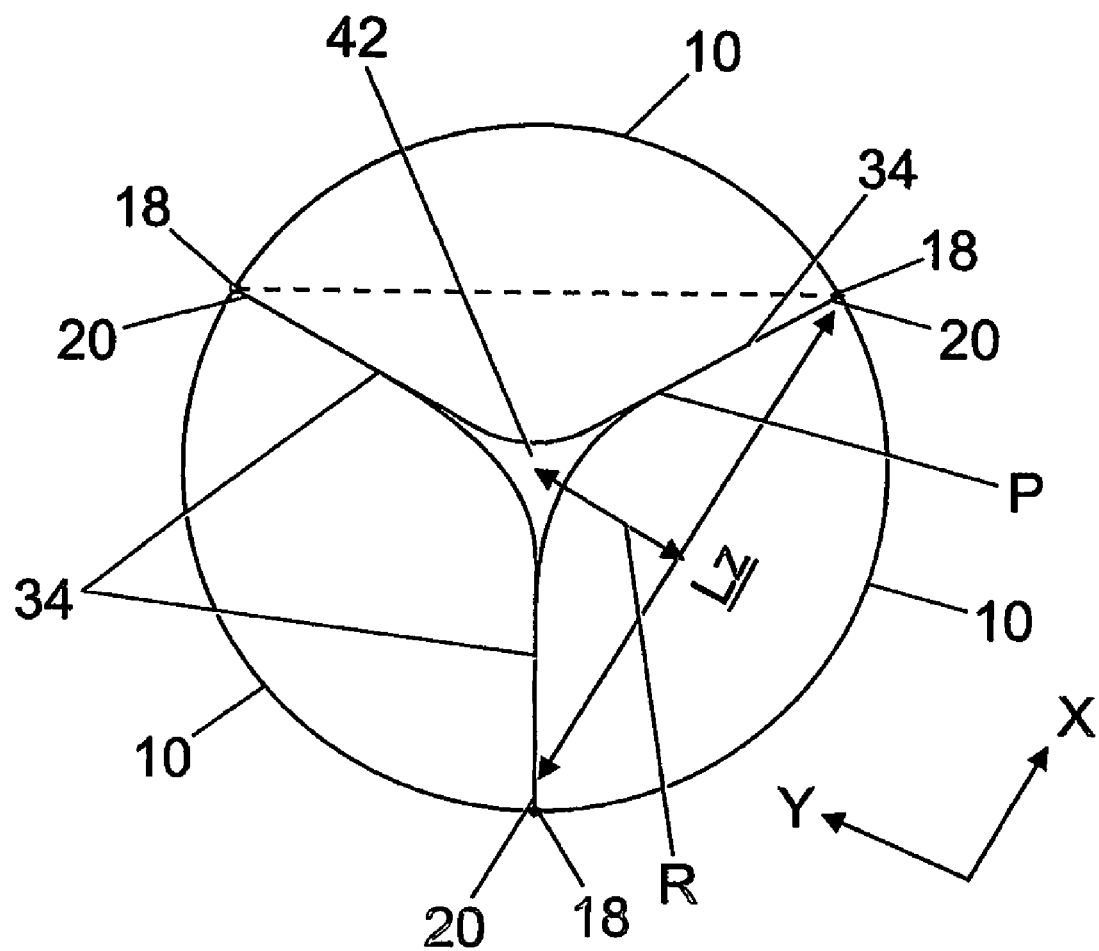
FIG. 6 is a plan view illustration of an embodiment of a trileaflet heart valve of the present invention.

As shown in FIG. 6 the material of the leaflet must extend between the posts 18 such that in a closed position the free edge of the leaflets 34 come together at point 42 to minimise regurgitation of blood through the valve.

This circumferential length (XY) can be mathematically defined using a parabolic function.

Function of a parabola $$Y_z = \left(\frac{4R}{L_z^2}\right) x \cdot (L_z - x)$$

Wherein
$Y_z$=Y offset at a particular co-ordinate X and Z
R=parabolic maximum
$L_z$=straight line distance between a first post and a second post of the frame at a height Z
X=distance from origin of post towards another post To calculate the circumferential length (XY) at a height point of the posts for a leaflet defined in the circumferential (XY) direction by a parabolic function the following function can be used:

$$\text{length of parabolic curve} = \int_0^t \sqrt{1 + \left(\frac{dy}{dx}\right)^2}\, dx$$

This allows a circumferential length (XY) to be determined at each height point in Z.

Figure 10:
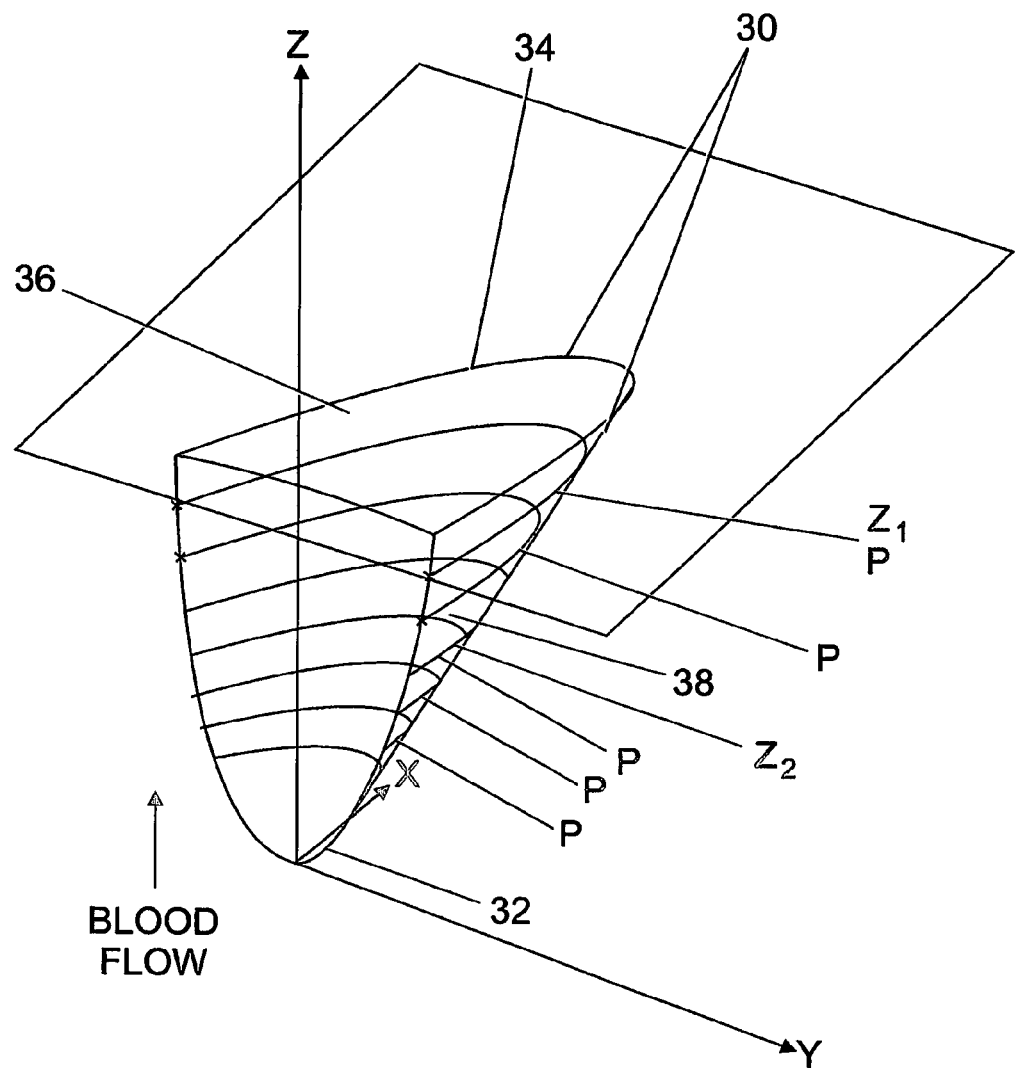
FIG. 10 is an illustration of an embodiment of one leaflet according to the present invention.
Figure 11A:
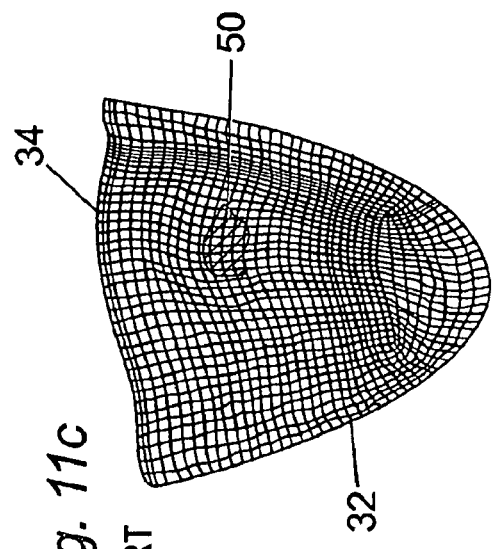
FIG. 11 is a diagrammatic representation of a prior art leaflet moving from a semi-closed (a) to successively more open position (b) and (c) to a fully open position (d) illustrating the formation of a bubble or buckle.
Figure 11C:
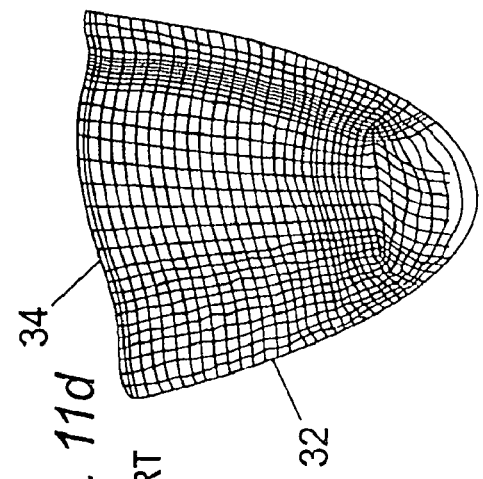
Figure 11B:
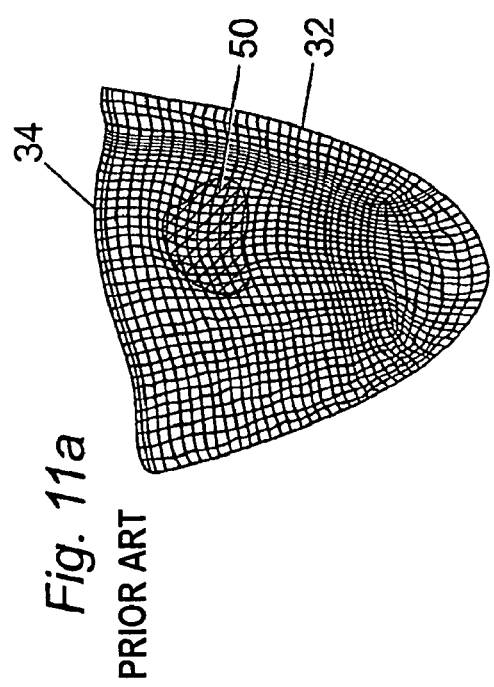
Figure 11D:
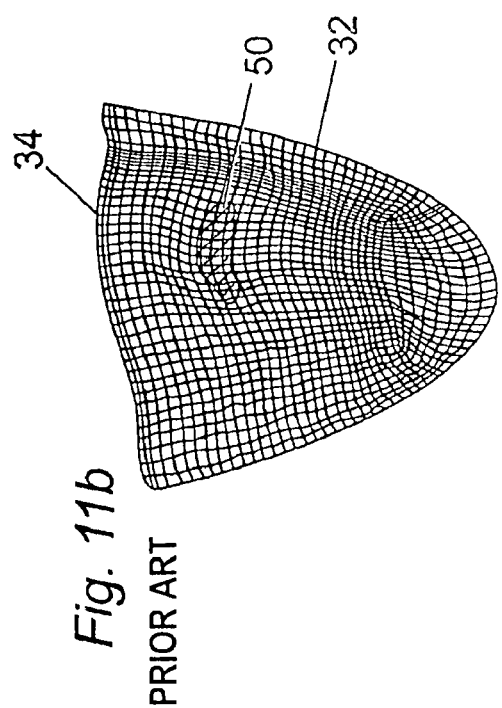

Thus as shown in FIG. 10 the circumferential length (XY) can be determined at Z1, Z2, Z3 . . . Zn.

The length of the leaflet in the circumferential direction (XY) is calculated and repeated in the radial direction (Z) to provide the complete geometry of the leaflet.

As the dimensions of the scallop edge 32 of the frame 10 as defined by the posts 18 of the frame can be determined by measuring the frame, then the straight line distance between a first post and a second post of the frame at a height Z ($L_z$) for a leaflet 30 can be determined by measuring the distance between the two posts 18 at several height points in Z (where Z is a particular height along the posts). This post to post distance can then be used in the equation detailed above to generate a parabola (P) at each height point. In the embodiment shown, due to the scallop shape 32 defined by the posts 18 the circumferential length of the leaflet in XY will decrease moving from the first end at the tip 20 of the posts toward the second end of the frame 14 at the base of the posts. The more height points which are chosen, the more lengths (P) which can be calculated along Z. If a large number of height points are chosen the lengths determined by the parabolic function moving from the tip of the posts to the base will vary in a substantially linear fashion.

The leaflets 30 of a valve 8 which are of circumferential length (XY) as determined using the above parabolic function will meet at the free edge 34 of the leaflet 30, but will not meet significantly at points lower than the free edge 34. The meeting of the leaflets at the free edge allows regurgitation to be minimised without including excess material or a belly region 40 in the leaflets 30.

The circumferential length (XY) can be further adjusted to take account of factors which occur during cycling of the heart valve. These factors include inward movement of the posts 18 of the frame 10 due to pressure on the leaflets 30 during closing of the valve. The amount of inward movement of the posts 18 of the frame 10 is influenced by the rigidity of the frame 10 and the pressure exerted on the valve. The tips 20 of the posts 18 of the frame 10 move to a greater extent than the base of the posts and as the scallop geometry between the posts 18 of the frame 10 is accurately known this differential movement can be taken into account when determining the optimal circumferential length (P) of XY in the leaflet 30.

In addition to the posts 18 of the frame 10 moving toward each other during closure, the posts 18 also move towards the centre point 42 where the leaflets meet or the point of coincidence. The circumferential length XY of the leaflet can be adjusted to account for this movement.

The material of the leaflet 30 typically has some degree of elasticity and will stretch in response to blood flow pressure. This stretching can again be taken into account in determining the lengths of the leaflet 30 to ensure that a belly region 40 of the valve is minimised.

Figure 8A:
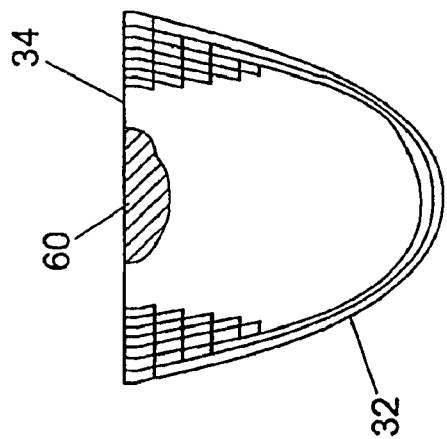
FIG. 8a shows the principal stress envelope present in a prior art heart valve leaflet.

As shown in FIG. 8a, analysis of the stresses over time incurred by heart valves during the cycling process has revealed that the principal area of stress 60 in existing cardiac valves is found close to the midpoint of the free edge of the leaflets.

Figure 8B:
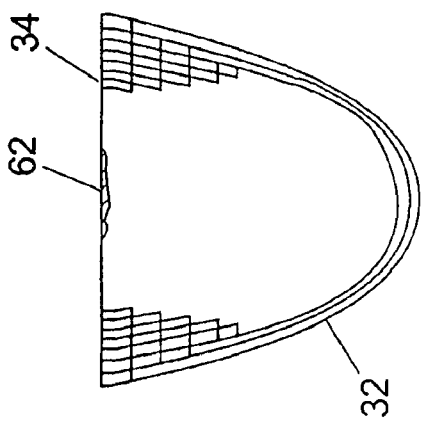
FIG. 8b shows the strain energy release present in a prior art heart valve leaflet in the X axis from a closed to open position.
Figure 8C:
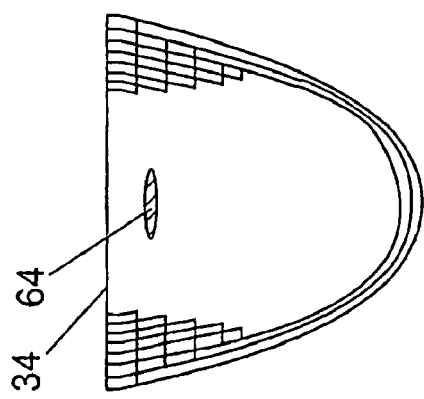
FIG. 8c shows the strain energy release present in a prior art heart valve leaflet in the Y axis from a closed to open position.
Figure 8D:
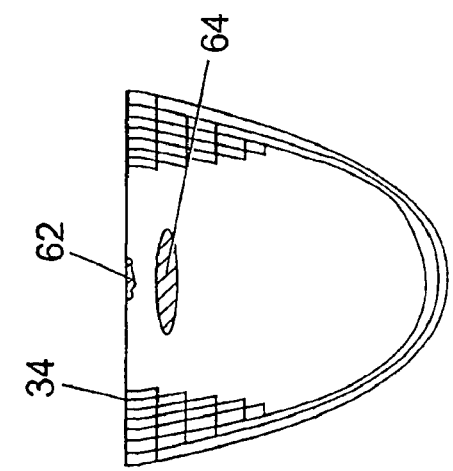
FIG. 8d shows the resultant strain energy release present in a prior art heart valve during cycling from a closed to open position.

Using the data from FIG. 8a, strain energy release in X and Y, as shown in FIGS. 8b and 8c respectively can be determined. FIG. 8b shows that leaflets of the prior art have a vertical predisposition to defect propagation 62 at the free edge 34. FIG. 8c indicates that leaflets have a predisposition to defect in the lateral dimension, at an area 64 in the leaflet 30 lower than the free edge of the leaflet 34, the lower area being located above the central portion of the leaflet. In tests during cycling of cardiac valves it has been found that over time, the stress in this lower area promotes failure of defects in the material to occur. These defects can cause valve failure.

The present invention has shown that analysis of the dynamics of existing valves during the cycling process has determined that the stress in this lower area is caused by the leaflets requiring to change the direction of their surface curvature during cycling.

In particular, as shown in FIG. 11, on cycling from a closed to an open position a region lower than the free edge forms a bubble like formation or buckle 50 on the surface of the leaflet which is opposite in direction to the curvature of the surface of the rest of the leaflet.

On moving from the closed to open position, the bubble like formation 50 is forced to become inverted such that it projects in an opposite direction causing a whip like action in the leaflet 30. This whip like action promotes high stresses in the area lower than the free edge 34 of the leaflet, as shown in FIGS. 8a, 8b, 8c and 8d.

Figure 9A:
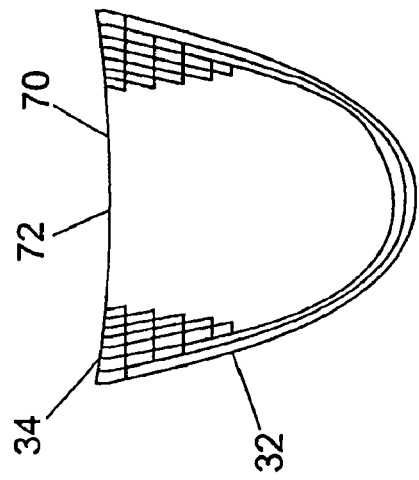
FIG. 9a shows the principal stress envelope present in an embodiment of a heart valve according to the present invention.
Figure 9B:
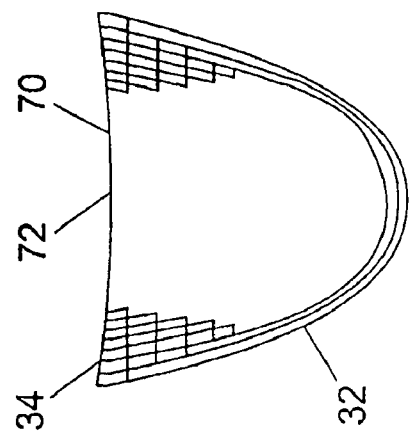
FIG. 9b shows the strain energy release present in an embodiment of a heart valve according to the present invention in the X axis from a closed to open position.
Figure 9C:
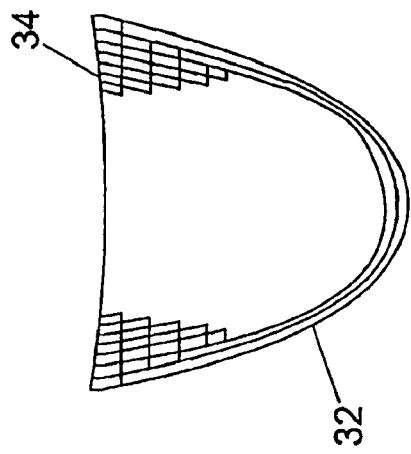
FIG. 9c shows the strain energy release present in an embodiment of a heart valve leaflet according to the present invention in the Y axis from a closed to open position.
Figure 9D:
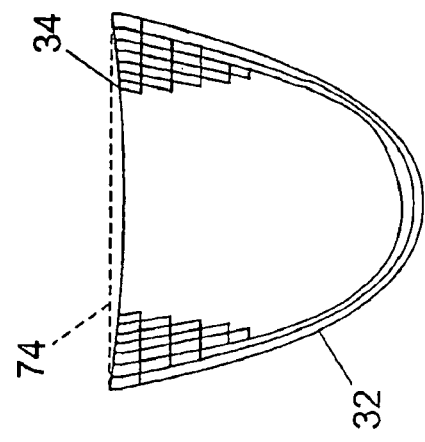
FIG. 9d shows the resultant strain energy release present in an embodiment of a heart valve leaflet according to the present invention during cycling from a closed to open position.

The inventor has surprisingly determined, as shown in FIG. 9a, that the principal stress envelope in relation to the valve as described in the present application, wherein the circumferential length XY of the leaflet at any point in Z is defined as a parabolic function, is decreased across the whole of the valve. In particular strain energy release in X and Y, as shown in FIGS. 9b and 9c respectively, in relation to the valve of the present invention indicates that a leaflet wherein the circumferential lengths XY are determined by a parabolic function has minimised predisposition to defect propagation in the lateral dimension at an area in the leaflet lower than the free edge of the leaflet and above the central portion.

A reduction in the predisposition to defect propagation in the lateral dimension at an area in the leaflet between the free edge of the leaflet and the central portion in the leaflet of the present invention is observed because there is less excess material and thus minimal belly in the leaflet of the present design.

On moving from the closed to open position a bubble like formation 50 is no longer created and thus a whip like action does not occur in the leaflet. As discussed, it is this whip like action which has been determined to promote high stresses in the area lower than the free edge of the leaflet. As illustrated by comparing FIGS. 8a and 9a, in contrast to the valves of the prior art, uniform principle stress distribution, is observed across the surface of the leaflet of the valve described in the present application.

Minimisation of the regions of stress in the leaflet, during cycling of the leaflet, will increase the durability of the leaflet.

Use of a parabolic function to determine the circumferential lengths XY of the leaflet at each height point in Z causes the vertical distribution of lengths of the leaflet to be substantially linear at the fully open and closed position.

As described above, it will be appreciated by those in the art that other functions with the addition of suitable modifying factors could be used to derive a function which substantially describes a parabola and which leads to the vertical distribution of lengths of the leaflet to be substantially linear at the fully open and closed position, but which is based on for instance an elliptical function.

As discussed, additional parameters may be included in the parabolic function used to determine the circumferential lengths XY of the leaflet. These additional factors may account for movement in the posts of the stent, elasticity of the leaflet material during movement of the leaflets from a closed to an open position or other factors which occur during cycling which influence the length of the leaflet require to allow closure.

The function described above explicitly determines lateral lengths of the parabolic curve at any height point in Z which is along a post of the frame. In view of this the above function can be applied to any diameter of valve or valves with different heights of posts, without the need for geometric scaling. This means that different dimensions of valves can be manufactured with the same leaflet geometry without further undue experimentation.

The surface contour of the leaflets 30 of the embodiment described are such that in a fully open position, the intersection of the leaflets of the valve perpendicular to the blood flow axis, forms a substantially cylindrical shape.

In addition to the above, it has also been determined that stress at the free edge of the leaflet, as shown in FIG. 8a, can be further reduced by trimming the free edge 34 of the leaflet in the longitudinal direction (Z) such that the free edge is substantially parabolic 70, with the maximum depth of the parabola being furthest from the notional untrimmed free edge 74. The maximum depth of the parabola is generally located at the midpoint of the free edge 72 (FIG. 9a). FIG. 9a shows the effect of introducing a parabolic curve in the vertical direction of the free edge. Comparison of FIGS. 8b, 8c and 8d with 9b, 9c and 9d shows that the strain energy release at the free edge is significantly reduced through the introduction of the parabola in the longitudinal direction (Z).

Ideally the notional free edge 74 is trimmed in a parabolic curve, wherein the maximum depth 72 of the parabola 70 in the longitudinal direction toward the second end of the frame is between 50 μm to 1000 μm, more preferably 50 μm to 500 μm, even more preferably 50 μm to 100 μm lower than the notional straight line 74 between the ends of the parabola.

A different shape of cut, trim or notch can be introduced in the free edge to decrease the stress at the free edge. However, particular shapes of cuts, trims or notches may introduce defects into the leaflet which would decrease the leaflets durability to stress. A parabolic trim as described is therefore advantageous in that focal points of stress are not introduced to the free edge of the leaflet. Cuts, trims and notches which do not create bending stresses at localised points on the free edge are preferable.

In one embodiment a parabolic cut may be made using an ultrasonic cutting device. As shown in FIG. 1, in one embodiment the ultrasonic cutting device comprises an ultrasonic transducer (100); a blade (110); and attachment means (120) to enable detachable attachment of the cutting blade to the transducer. The blade has two arcuate cutting edges which meet at a point to form the terminal end of the blade. In this embodiment the stylus is not present. The ultrasonic cutting device is mounted on the mounting table (130) by means of a clamping assembly (140). The clamping assembly includes an upright member (150) that extends from a first end perpendicularly from the mounting table, a support member (160) that extends laterally from the upright member and is held relative to the upright member by a fixing block (170), and a clamp (180) which secures the ultrasonic cutting device to the clamp support member. The clamp support member is slideably moveable up and down a portion of the upright member by turning of an adjusting screw (190). In addition, the clamp support member is slideably moveable laterally in relation to the upright member, this movement being effected by the rotation of a second adjusting screw (200). The clamp support member is located between the fixing block and a securing plate (210). The securing plate can be moved towards the upright member to secure the clamp support member at a suitable position.

Figure 16:
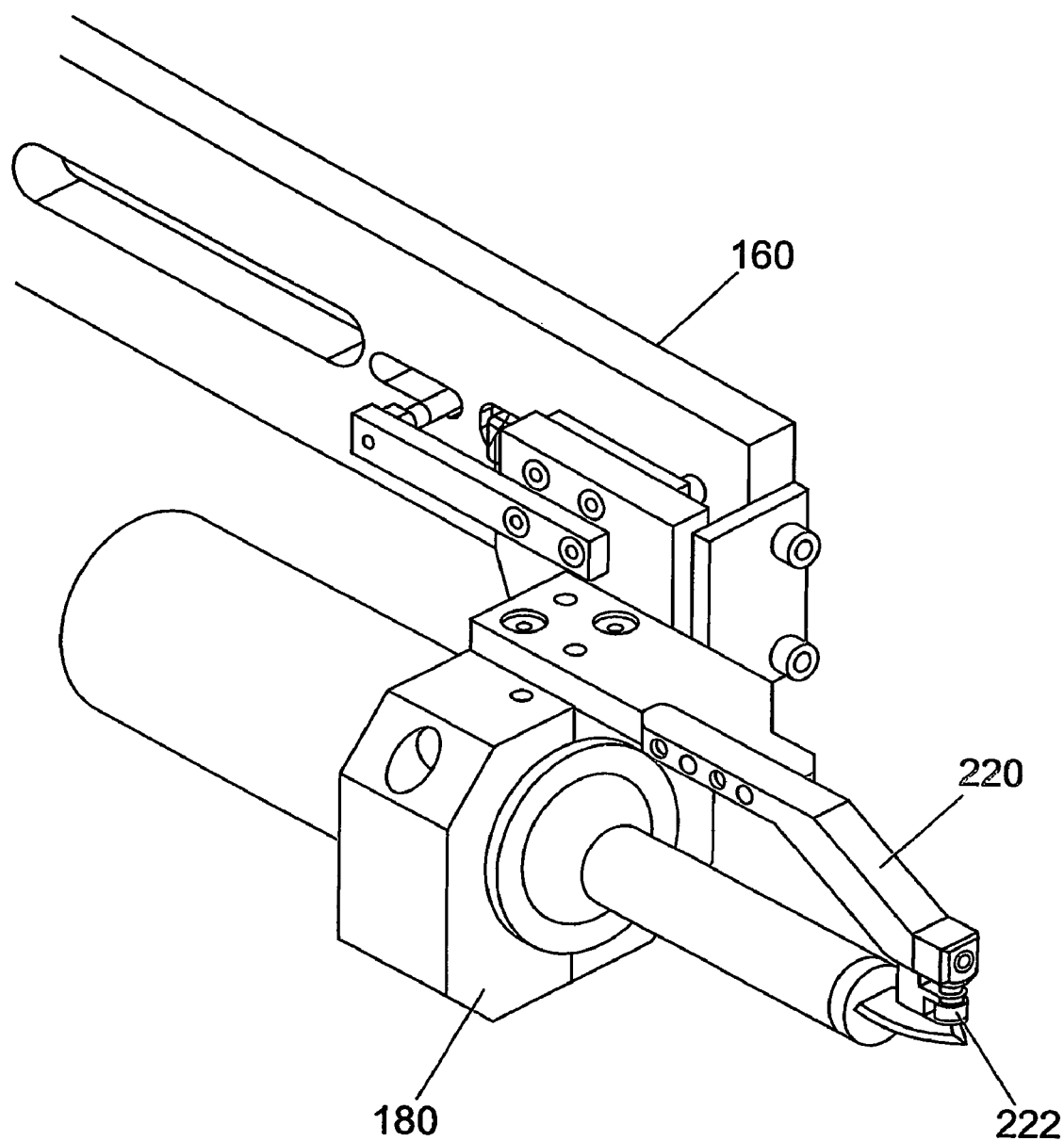
FIG. 16 is a view of the cutting apparatus of an ultrasonic cutting device.

As shown in FIG. 16 an arm (220) can extend from the clamp (180) to the cutting blade. A ball bearing (222) is rotatably mounted at one end of the arm and is positioned just above, but not in contact with, the blade. In use the ball bearing is in contact with the surface of the article to be cut and its position controls the extent of blade penetration into the article.

Figure 17:
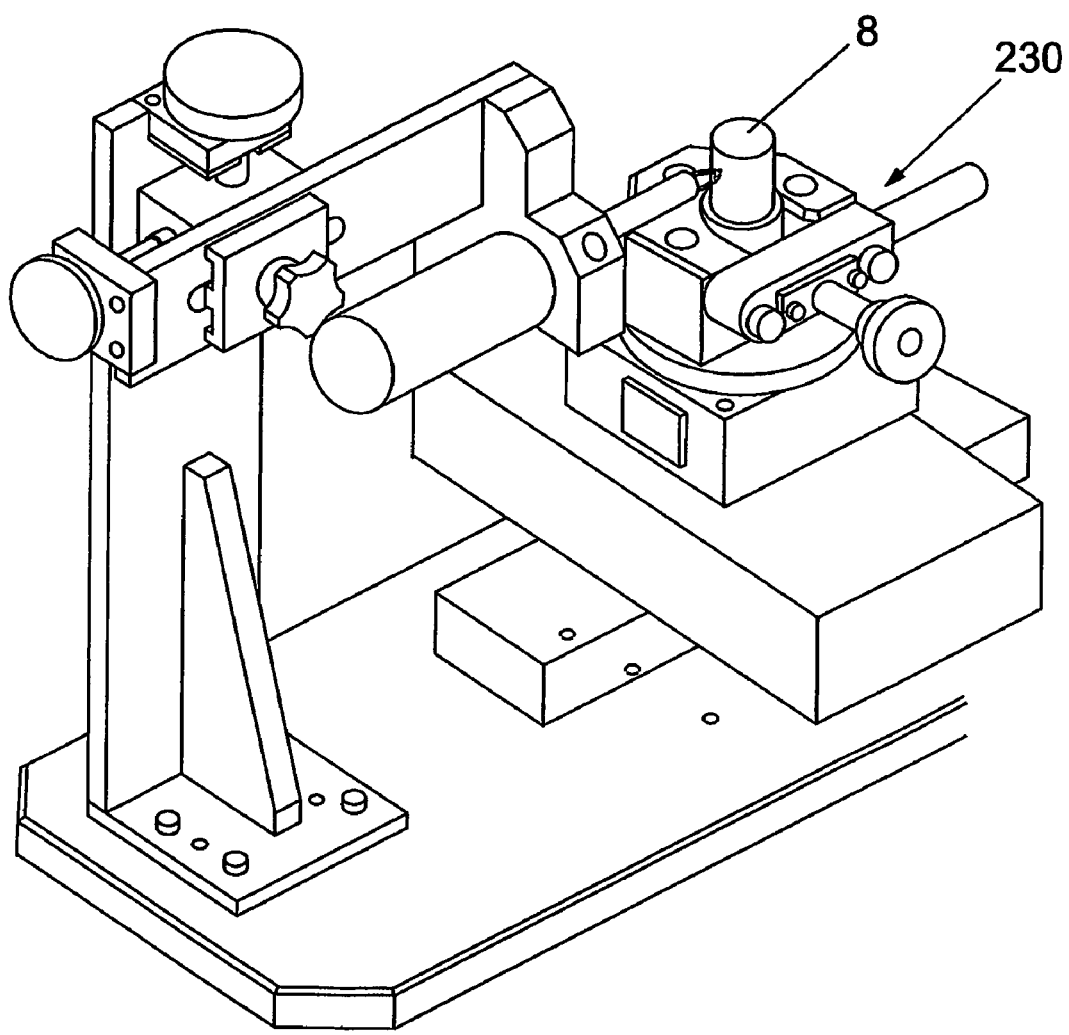
FIG. 17 is a perspective view of an ultrasonic cutting apparatus according without a stylus.
Figure 18:
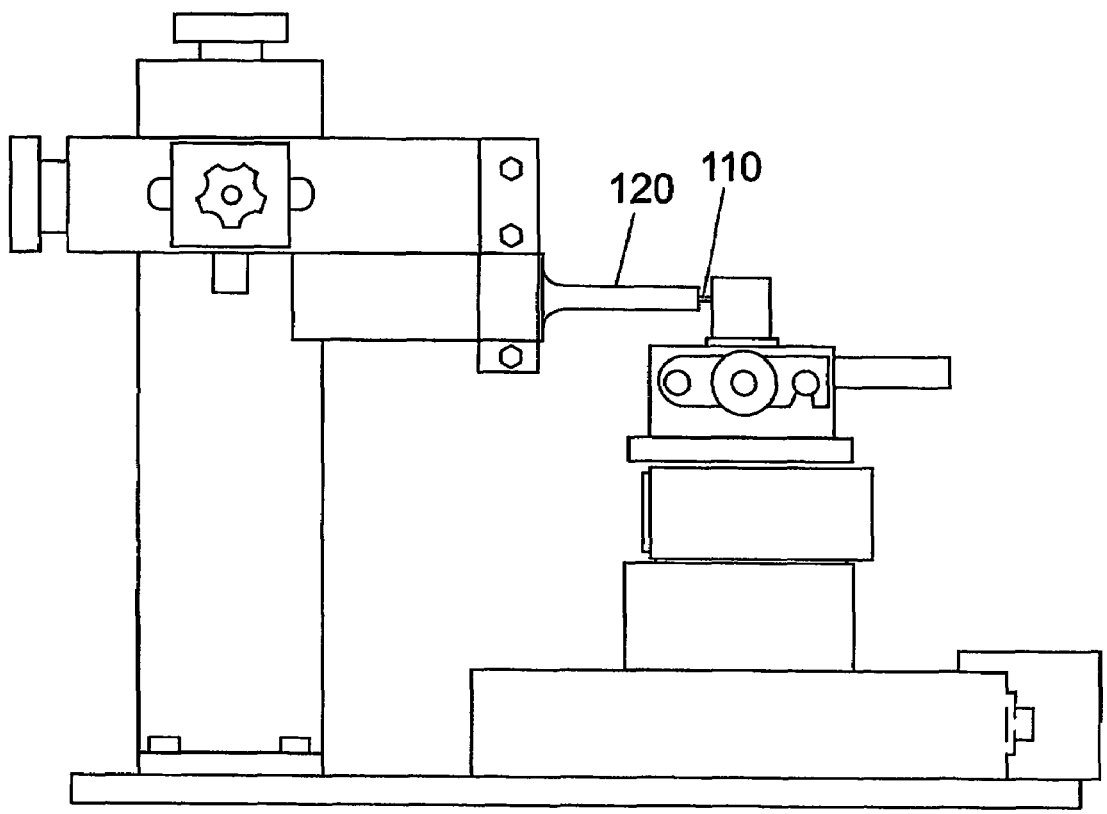
FIG. 18 is a side view of ultrasonic cutting apparatus without a stylus.

FIG. 17 shows a perspective view of the cutting apparatus in position for operation without the stylus guide. The heart valve leaflet to be cut is mounted on a 3-axis drive unit (230). This drive unit may be driven by electric motors. FIG. 18 is a side view of the embodiment shown in FIG. 17.

In the embodiment of FIGS. 17 and 18, movement of the drive means causes the heart valve leaflet to be cut to be brought into contact with the blade. By accurate positioning of the heart valve leaflet to be cut, the cutting process may be accurately repeated. A set pattern can then be followed and may be instructed by a computer which drives the drive means.

Leaflets of the geometry described herein can be produced using methods known in the art such as injection moulding, reaction injection moulding, compression moulding or dip moulding.

In one embodiment the heart valve leaflets may be made by inverted dip moulding. As shown in FIG. 14a an embodiment of inverted dipping apparatus may comprise a platform (1000) holding a forming element (1110). A housing (1130) is sealed to the platform to form a closed chamber (1140). The housing comprises side walls (1150) and a ceiling (1160) and is provided with inlet means (1170) which can be closed by valve (1180).

The platform is adapted to hold at least one forming element. Preferably the platform is adapted to hold one forming element. By hold means the forming element is secured to the platform so that it will remain in place even upon inversion or rotation of the platform. Preferably the forming element is releasably held on the platform.

The forming element has a shape so that when coated with the moulding solution it will produce an article of the desired size and shape. The forming element may comprise a core holding a frame which when coated with the moulding solution will produce a leaflet of the desired size and shape.

Figure 14C:
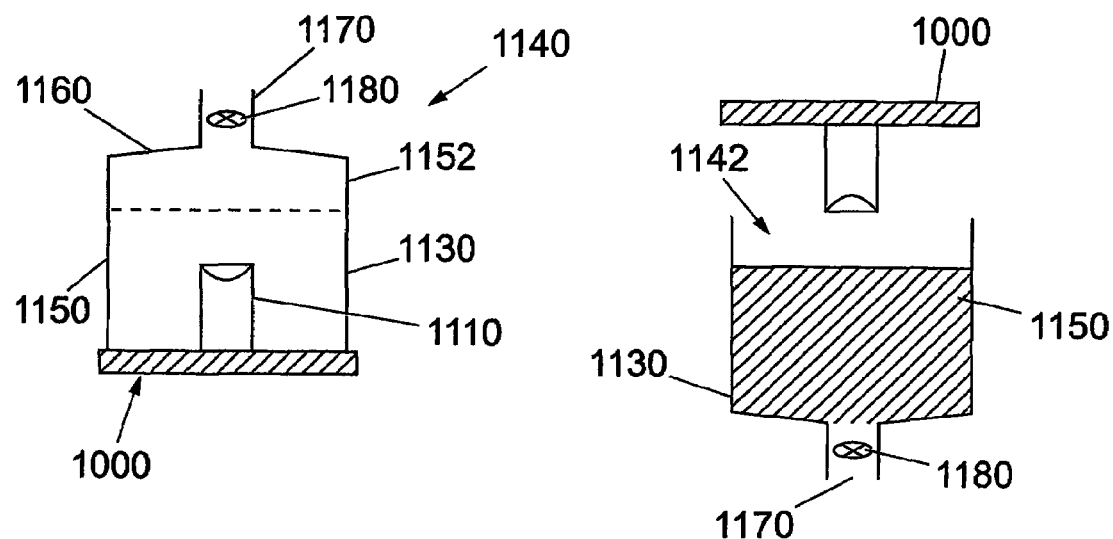
FIG. 14c shows a cross sectional view of a forming element suitable for use in the moulding apparatus of the present invention.
Figure 14C:
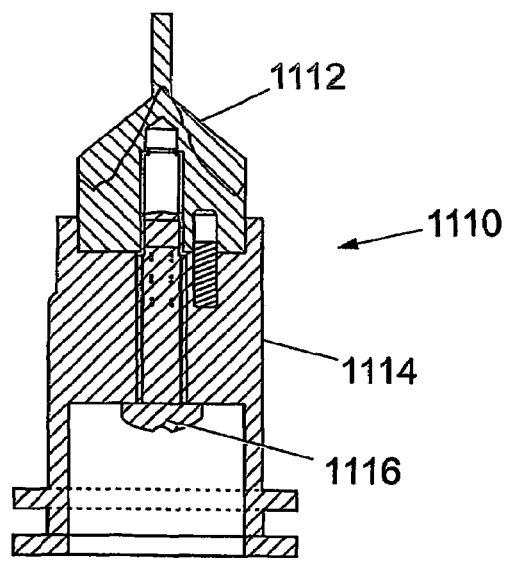
Figure 15:
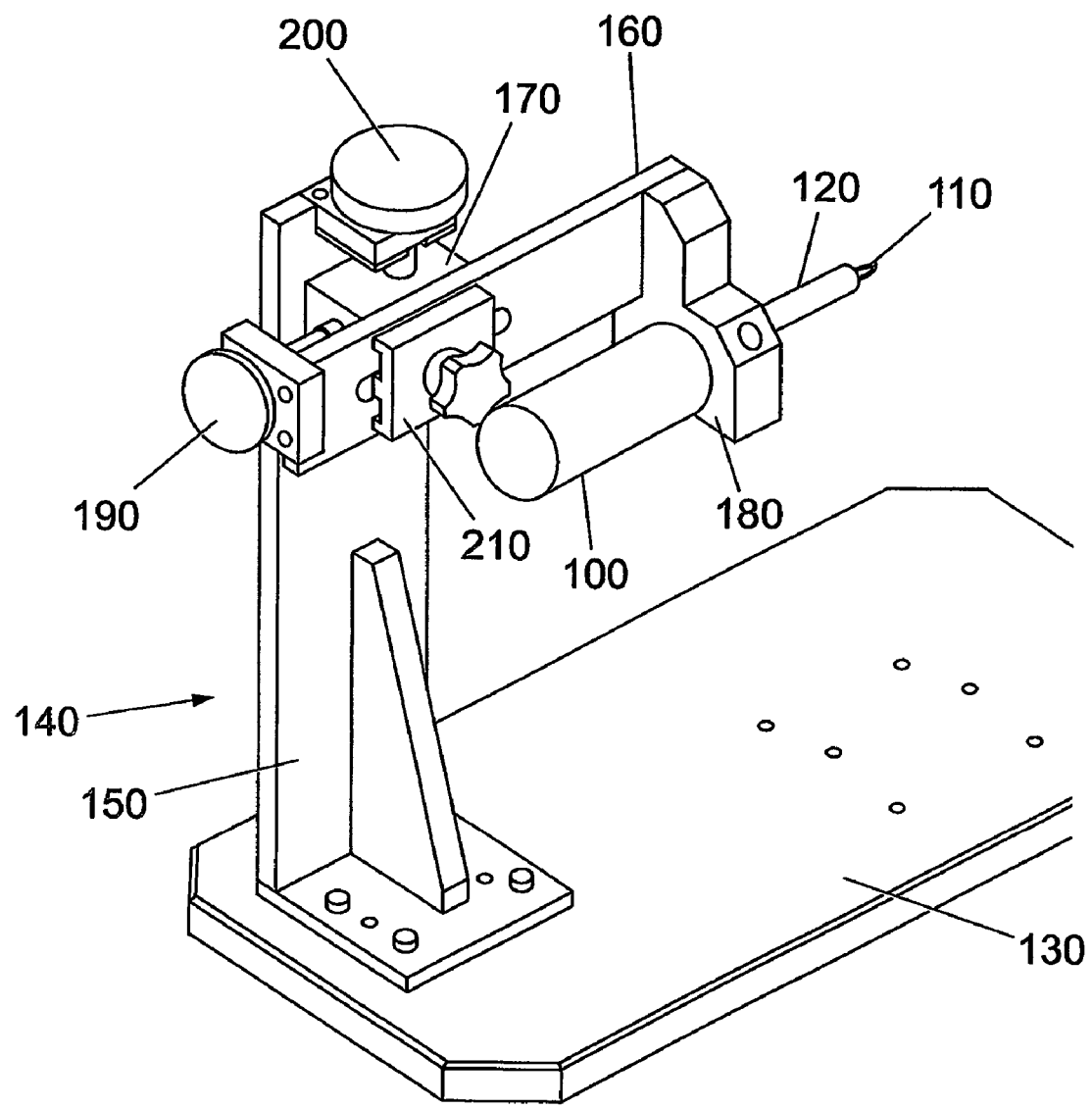
FIG. 15 is a perspective view of an ultrasonic cutting device mounted on a mounting table.

In a preferred embodiment, the forming element (1110) is of two-part form, as is shown in FIG. 14C. The forming element comprises a frame mount (1112) fixed to a base portion (1114). A frame 8, for a heart valve prosthesis, can be mounted on the frame mount 1112. The frame mount is fixed to the base by fixing means for example a screw (1116) or any suitable fixing means such as a bayonet fitting or push fit fitting. The frame mount is removable from the base portion.

A frame mount and base portion, (two part forming element) may be used during leaflet construction, the frame mount being suitably shaped to a frame to be mounted on the frame mount and allow the production of the leaflets by dip moulding. The frame mount can also be used to hold the frame and leaflets during subsequent cutting of the valve leaflets. The frame mount is releasably attachable to the base forming element portion such that the frame mount portion can be removed from the base portion so that the base portion may be reused. The frame mount portion may be releasably attachable to the base portion by a screw. Should the frame mount be damaged during the cutting stage the frame mount can be discarded while retaining the base portion and thus only a part and not the entire forming element need be replaced. In addition, different types of forming element mounts capable of mounting frames of different diameters or with different valve leaflet shapes can be fixed to the same base portion thus reducing the need for complete forming elements.

The housing (1140) has an open end (1142) so that when placed on the platform (1000) the forming element can extend into the housing.

The housing is of a shape and size so that it fits over the forming element (1110) and has the capacity to hold enough moulding solution to coat the forming element. The housing has a ceiling (1160) which is the part of the housing opposite to the platform. The housing may have any suitable shape, for example it may be a cylinder having one closed and one open end, with its closed end being the ceiling.

Typically the platform and the housing are constructed from steel.

The apparatus is provided with means for inverting the closed chamber. The inverted and open chamber is shown in FIG. 14b. Inversion of the housing may be provided by means for rotating the platform about a horizontal axis. In one embodiment, the platform is rotatable about a horizontal axis through the horizontal plane of the platform. This may be achieved by having the platform pivotally supported on a frame. The frame may comprise lateral pins which extend laterally from the frame into the platform so that the platform can rotate around them. In an alternative embodiment, the housing is rotatable about a horizontal axis in the horizontal plane of the open end of the housing. This may be achieved by having the housing pivotally supported on a frame. The frame may comprise lateral pins which extend laterally from the frame into the housing so that the housing can rotate around them.

Preferably inversion of the closed chamber is effected by drive means including a hand crank and an electric motor.

The closed chamber has closeable inlet means for introducing the moulding solution to the closed chamber. The inlet means may be closeable by means of a valve. The inlet means are preferably an opening in the ceiling of the housing and are provided with a pipe in connection with a central reservoir of moulding solution. In one embodiment the platform is provided with the inlet means. The inlet means may alternatively be provided in one of the side walls of the housing so that it will be in a position close to the platform in the closed chamber. In this embodiment the moulding solution may be pumped from a reservoir into the closed chamber via the inlet means. This latter embodiment is preferred when more viscous moulding materials are being used.

Preferably the inlet means and/or the outlet means are heated. The moulding solutions generally used in the moulding of surgical implants are generally viscous in nature and this viscous nature can make the movement of the moulding solutions through the inlet and outlet means difficult to achieve. Heating means can be incorporated in the moulding apparatus and used to heat both the housing and the inlet and outlet means. The raised temperatures of the moulding solutions make these solutions less viscous allowing easier movement of the solutions through inlet and outlet tubes.

The housing has closeable outlet means. Preferably an opening/pipe in the ceiling of the housing forms the outlet means. When the housing is inverted then the moulding solution can be drained through such an opening/pipe under the force of gravity. The outlet means may be closeable by means of a valve.

Preferably, as in the embodiment shown in FIGS. 14a and 14b, the outlet means is also the inlet means.

In operation, a forming element is releasably secured to the platform and a housing is placed over the forming element and sealed to the platform. The closed chamber thus formed should be in a position whereby the forming element is upright. Moulding solution is introduced into the chamber through the inlet means until it reaches a level above the forming element, e.g. level (1152) indicated in FIG. 14a. At this stage the inlet means is closed by means of valve (1180). After a suitable period of time, the platform, and thus the closed chamber, is inverted by rotating, in this case, the platform around a horizontal axis. The inverted chamber is then left for a suitable period of time before the housing/platform seal is broken and the housing is lowered. This exposes the now-coated forming element in an inverted position. This can be seen in FIG. 14b. The moulding solution can then be drained from the housing using the inlet means (1170) which doubles as outlet means in this embodiment. Alternatively the moulding solution can be drained from the housing before the housing/platform seal is broken. The coating on the forming element can now be dried/cured/treated appropriately.

As the closed chamber is a sealed system it is possible to exchange the air present in the interior of the closed chamber, when moulding solution is not present, with another solution or gas. The type of solution or gas with which the mould chamber can be filled prior to introduction of moulding solution can be chosen in line with manufacturing requirements. In this way, contact between the mould solution and moisture in the air can be avoided.

In one embodiment the apparatus comprises a plurality of platforms and a plurality of housings. In this embodiment, preferably all the inlet means are in connection with a central reservoir of moulding solution, with the inlet means and the reservoir forming a manifold. Preferably the manifold is heated. In this embodiment, preferably all the platforms are pivotally supported as a unit on a frame or all the housings are pivotally supported as a unit on a frame. Batch moulding carries the advantages of having greater consistency of results and of being more cost effective.

As discussed the circumferential length XY of the leaflet at any height point in Z along the post of the frame is explicitly provided by a parabolic function or a pseudo function used to describe a parabolic function. As is clear from FIGS. 1e, 1f and 1g, the manufacture of valve leaflets in the closed position, as described herein, by dip moulding or injection techniques would be difficult as the free edges of the leaflets contact each other. Although a forming element could be provided in which the valve leaflets were produced in the open position, it is more desirable to form the leaflet in a neutral position between the two extremes of fully open or fully closed.

One method of forming the leaflets is to determine the length of the leaflet in the XY direction for each point in Z for a preferred shape of leaflet.

Figure 12:
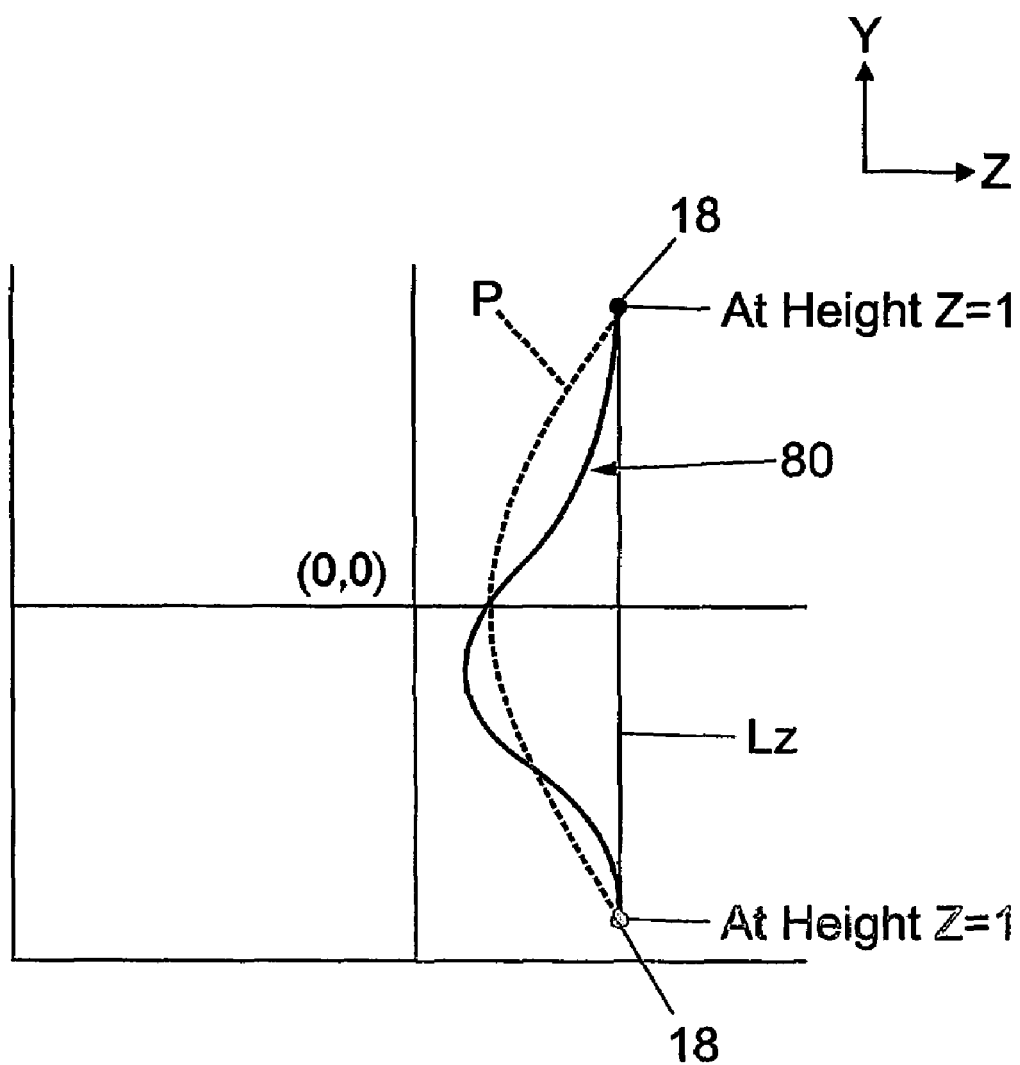
FIG. 12 illustrates a shape of the leaflet being defined by a first wave further to determination of the circumferential length of the leaflet.

On determining the length of the leaflet at each point in Z to minimise the formation of a belly in the leaflet and using appropriate correction factors to determine a final XY length at that point in Z, a wave function can be applied to the leaflet at that point in Z. As shown in FIG. 12 the wave function will change the shape of the leaflet at that point in Z from a parabolic curve to a desired cast shape, but the length of the leaflet as determined by the initial parabolic shape will be maintained and following manufacture of the valve, closure of the valve, will cause the leaflet to adopt a parabolic shape again at each point in Z.

The wave shape of the leaflet is used to provide a forming element with leaflet forming surfaces of the shape as defined by the waves arranged in Z for casting of leaflets.

The valve is thus produced such that in a cast position the leaflet is in neutral position, intermediate the open and closed position in the absence of fluid pressure being applied to the leaflets. Production of the valve in the neutral position means that the leaflets are substantially free of bending stresses in this position.

The shape of the forming element, on which the leaflet is formed, can be defined by one wave function, or several wave functions which together form a composite wave.

Regardless of the wave function used for the casting of the leaflet, the length of the leaflet is defined at each point in Z along the post of the scallop by a parabolic function or pseudo parabolic function as described above together with any correction factors.

The shape of the inner surface of the leaflets will substantially replicate the shape of the forming element. The shape of the outer surface of the leaflets will be similar to the shape of the inner surface, but variations will result e.g. from the properties of the polymer solution and techniques used to create the leaflet.

The leaflets of suitable length as defined by the parabolic function and any correction factors and of shape as defined by either a single or composite wave function are attached to a suitable frame. The construction of a suitable frame will be obvious to those skilled in the art. The frame can be made of a biocompatible polymer, metal or composite. The frame can be coated with polyurethane to allow integration of the leaflets.

Further to describing a first leaflet using the above function, the remaining two leaflets of this three leaflet embodiment can be determined by rotating the geometry about the Z axis through 120° and then through 240°.

Having formed the leaflets of the valve as described above these can then be trimmed to introduce a parabolic curve into the edge of the leaflet not attached to the frame (free edge) which extends horizontally between two posts. The maximum depth of the parabola being located between 50 μm to 1000 μm lower than the notional straight line between the ends of the parabola toward the portion of the leaflet which attaches the leaflet to the scallop portion of the frame.

Figure 13:
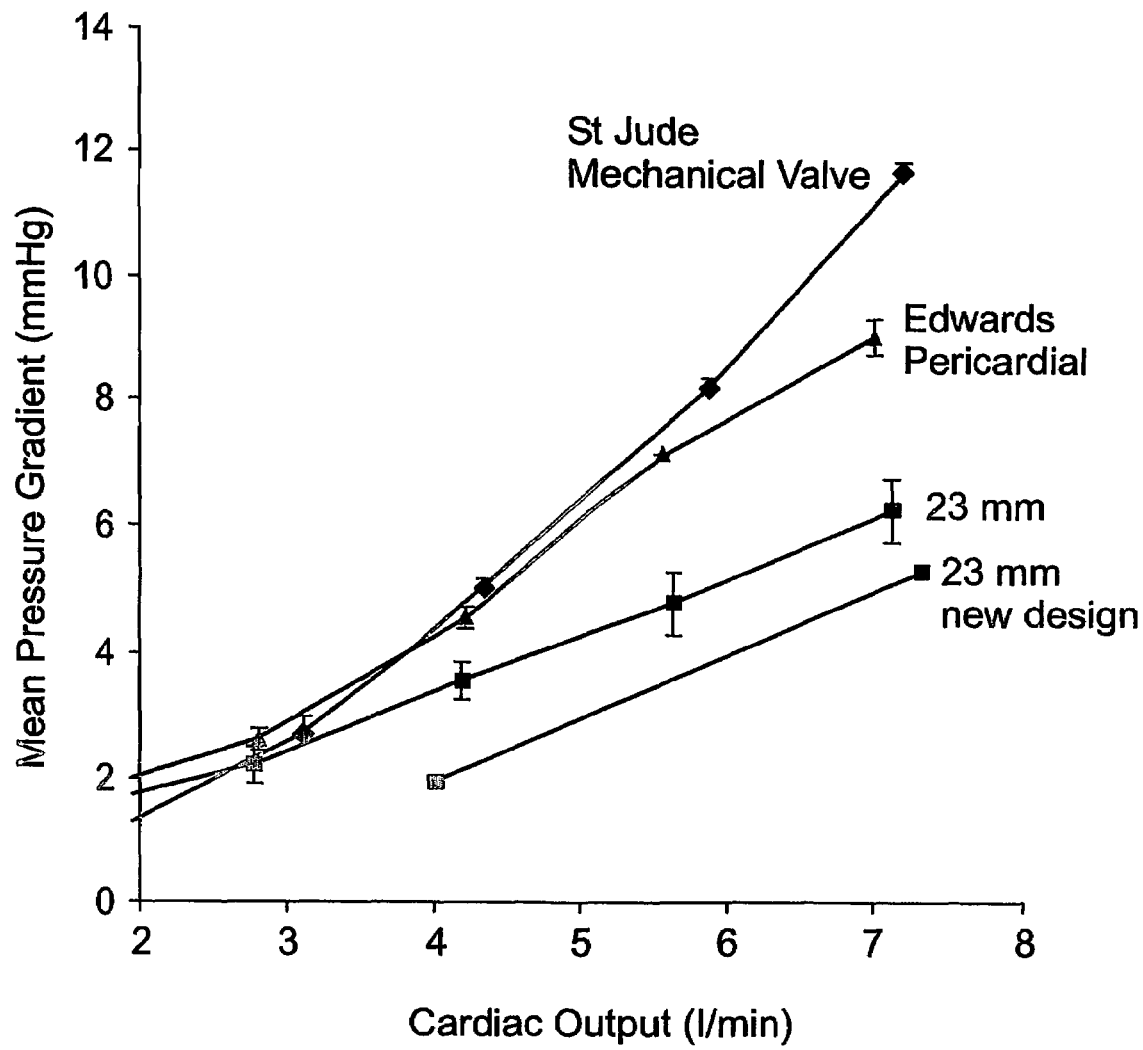
FIG. 13 is a graph of Cardiac Output (l/min) against mean Pressure Gradient (mmHg)

As shown in FIG. 13, surprisingly, in addition to reducing the lateral stress of the valve, determination of the length of the leaflet at each point in Z according to a parabolic function not only minimises the formation of a belly in the leaflet, but also reduces the pressure gradient required to open the valve from a closed position.

The opening of a cardiac valve to as wide an orifice as possible under minimal pressure gradients is a key parameter in the design of synthetic heart valves.

A valve of the present invention may be used in any required position within the heart to control blood flow in one direction, or to control flow within any type of cardiac assist device.

Modifications and improvements can be incorporated without departing from the scope of the invention.

The invention claimed is:

1. A cardiac valve comprising a frame and at least two flexible leaflets moveable between an open and closed position; wherein the frame comprises an annular portion defining an (XY) plane which, in use, is disposed substantially perpendicular to the blood flow, the frame having first and second ends, one of the ends defining at least two scalloped edge portions separated and defined by at least two posts, wherein said leaflet has first and second lateral edges each attached to a scalloped edge portion of a corresponding post of the frame, wherein the leaflet is formed such that the length of the leaflet between the lateral edges measured at each height (Z) along the lateral edges in an (XY) plane substantially perpendicular to the direction in which the height (Z) is measured is defined by a parabolic function wherein the lengths determined by the parabolic function vary in a substantially linear fashion with the height (Z) when the valve is in a closed position.

2. A cardiac valve as claimed in claim 1 wherein the parabolic function is defined by $$Y_z = \left(\frac{4R}{L_z^2}\right) x \cdot (L_z - x)$$

wherein
$Y_z$=Y offset at a particular co-ordinate X and Z
R=parabolic maximum
$L_z$=straight line distance between a first lateral edge for attachment to a corresponding post and a second lateral edge for attachment to second corresponding post at a height Z x=distance from origin of first corresponding post towards second corresponding post and the length of the parabola defined by the above is determined by $$\text{Length} = \int_0^t \sqrt{1 + \left(\frac{dy}{dx}\right)^2}\, dx.$$

3. A cardiac valve prosthesis comprising:

a frame and at least two flexible leaflets;

wherein the frame comprises an annular portion defining an (XY) plane which, in use, is disposed substantially perpendicular to the blood flow, the frame having first and second ends, one of the ends defining at least two scalloped edge portions separated and defined by at least two posts, each leaflet being attached to the frame along a scalloped edge portion and being movable between an open and a closed position;

wherein the leaflet is formed such that the length of the leaflet between the lateral edges measured at each height (Z) along the lateral edges in an (XY) plane substantially perpendicular to the direction in which the height (Z) is measured is defined by a parabolic function wherein the lengths determined by the parabolic function vary in a substantially linear fashion with the height (Z) when the valve is in a closed position;

each of the at least two leaflets having a blood inlet side, a blood outlet side and at least one free edge, the at least two leaflets being in a closed position when fluid pressure is applied to the outlet side such that the at least one free edge of a first leaflet is urged towards the at least one free edge of a second leaflet, and the at least two leaflets being in an open position when fluid pressure is applied to the blood inlet side of the at least two leaflets such that the at least one free edge of the first leaflet is urged away from the at least one free edge of the second leaflet.

4. The cardiac valve prosthesis as claimed in claim 3 wherein the parabolic function defining the length of a leaflet in the circumferential direction (XY) between the posts at any position along the longitudinal axis (Z) of a post is defined by $$Y_z = \left(\frac{4R}{L_z^2}\right) x \cdot (L_z - x)$$

Wherein $Y_z$=Y offset at a particular co-ordinate X and Z

R=parabolic maximum $L_z$=straight line distance between a first post and a second post of the frame at a height Z x=distance from origin of post towards another post and the length of the parabola defined by the above is determined by $$\text{Length} = \int_0^t \sqrt{1 + \left(\frac{dy}{dx}\right)^2}\, dx.$$

5. The cardiac valve prosthesis as claimed in claim 3 comprising three leaflets.

6. The cardiac valve prosthesis as claimed in claim 3 wherein the frame is a collapsible stent.

7. The cardiac valve prosthesis as claimed in claim 3 wherein the length of the free edge of the leaflet is increased relative to the length of the leaflet in an (XY) plane substantially perpendicular to the blood flow by configuring the free edge as a parabolic shape in the height (Z) of the leaflet.

8. The cardiac valve prosthesis as claimed in claim 7 wherein the free edge of the leaflet is trimmed to provide a parabolic shape in the height (Z) of the leaflet such that the maximum depth of the parabola is furthest from the notional midpoint of the untrimmed free edge.

* * * * *